US007199134B2

(12) United States Patent
Breslow et al.

(10) Patent No.: US 7,199,134 B2
(45) Date of Patent: Apr. 3, 2007

(54) HYDROXAMIC ACID COMPOUNDS AND METHODS OF USE THEREOF

(75) Inventors: Ronald Breslow, Englewood, NJ (US); Thomas A. Miller, Brookline, MA (US); Sandro Belvedere, New York, NY (US); Paul A. Marks, Washington, CT (US); Victoria M. Richon, Wellesley, MA (US); Richard A. Rifkind, New York, NY (US)

(73) Assignees: Sloan-Kettering Institute for Cancer Research, New York, NY (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/817,688

(22) Filed: Apr. 1, 2004

(65) Prior Publication Data
US 2004/0266818 A1 Dec. 30, 2004

Related U.S. Application Data

(60) Provisional application No. 60/459,826, filed on Apr. 1, 2003.

(51) Int. Cl.
*C07D 215/38* (2006.01)
*C07D 215/36* (2006.01)
*A61K 31/47* (2006.01)
*A61K 31/44* (2006.01)

(52) U.S. Cl. .................. 514/312; 546/171; 546/172; 514/313; 514/314

(58) Field of Classification Search ............... 546/171, 546/172; 514/312, 313, 314
See application file for complete search history.

(56) References Cited

U.S. PATENT DOCUMENTS

| 2,279,560 A | 4/1942 | Dietrich |
| 2,346,665 A | 4/1944 | Cupery |
| 2,895,991 A | 7/1959 | Randall et al. |
| 3,450,673 A | 6/1969 | McKillip |
| 3,632,783 A | 1/1972 | Stonis |
| 3,875,301 A | 4/1975 | Windheuser |
| 4,056,524 A | 11/1977 | Walker |
| 4,442,305 A | 4/1984 | Weitl et al. |
| 4,480,125 A | 10/1984 | Haas |
| 4,522,811 A | 6/1985 | Eppstein et al. |
| 4,537,781 A | 8/1985 | Darling |
| 4,611,053 A | 9/1986 | Sasa |
| 4,614,815 A | 9/1986 | Cognigni et al. |
| 4,801,748 A | 1/1989 | Murahashi et al. |
| 4,863,967 A | 9/1989 | Hall et al. |
| 4,882,346 A | 11/1989 | Driscoll et al. |
| 4,935,450 A | 6/1990 | Cone, Jr. |
| 4,983,636 A | 1/1991 | Takeuchi et al. |
| 5,055,608 A | 10/1991 | Marks et al. |
| 5,175,191 A | 12/1992 | Marks et al. |
| 5,330,744 A | 7/1994 | Pontremoli et al. |
| 5,366,982 A | 11/1994 | Dereu et al. |
| 5,369,108 A | 11/1994 | Breslow et al. |
| 5,668,179 A | 9/1997 | Breslow et al. |
| 5,700,811 A | 12/1997 | Breslow et al. |
| 5,773,474 A | 6/1998 | Breslow et al. |
| 5,846,960 A | 12/1998 | Labrie |
| 5,932,616 A | 8/1999 | Breslow et al. |
| 6,087,367 A | 7/2000 | Breslow et al. |
| 6,511,990 B1 * | 1/2003 | Breslow et al. ............ 514/314 |
| 2003/0235588 A1 | 12/2003 | Richon et al. |
| 2004/0087657 A1 | 5/2004 | Richon et al. |
| 2004/0092558 A1 | 5/2004 | Klimko et al. |

FOREIGN PATENT DOCUMENTS

| WO | WO 01/18171 | * 3/2001 |
| WO | WO 03/032921 | 4/2003 |

OTHER PUBLICATIONS

Archer et al. (1998). *PNAS* 95: 6791-6796.
Brown et al. (1986). *23-Aliphatics* 105: 605. (From *Synth. Commun.*, 1985, 15: 1159-1164, Abstract No. 78501v).
Brown et al. (1986). *Inorganic Chemistry* 25: 3792-3796.
Chun et al. (1986). *Cancer Treatment Reports* 70: 991-996.
Cohen et al. (1999). *Anticancer Res.* 19: 4999-5006.
Curtin, M. (2002). *Expert Opin. Ther. Patents* 12: 1375-1384.
Das et al. (1984). "Synthesis of Some Dihydroxamic Acid Siderophores." *Chemical Abstracts* 101: 582. (From *J. Chem. Eng. Data*, 1984, 29: 345-348, Abstract No. 54665t).

(Continued)

*Primary Examiner*—D. Margaret Seaman
(74) *Attorney, Agent, or Firm*—Ivor R. Elrifi, Esq.; Mintz Levin Cohn Ferris Glovsky and Popeo PC

(57) ABSTRACT

The present invention relates to a novel class of hydroxamic acid derivatives having at least two aryl containing groups, at least one of which is a quinolinyl, isoquinolinyl or benzyl moiety, linked to the hydroxamic acid group through a methylene chain. The hydroxamic acid compounds can be used to treat cancer, for example, brain cancer. The hydroxamic acid compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present are useful in treating a patient having a tumor characterized by proliferation of neoplastic cells. The compounds of the invention are also useful in the prevention and treatment of TRX-mediated diseases, such as autoimmune, allergic and inflammatory diseases, and in the prevention and/or treatment of diseases of the central nervous system (CNS), such as neurodegenerative diseases.

38 Claims, No Drawings

OTHER PUBLICATIONS

Dressel et al. (2000). *Anticancer Res. 20*: 1017-1022.
Egorin et al. (1987). *Cancer Res. 47*: 617-623.
Fibach et al. (1977). *Cancer Res. 37*: 440-444.
Finnin et al. (1999). *Nature 401*: 188-193.
Grunstein et al. (1997). *Nature 389*: 349-352.
Haces et al. (1987). *J. Med. Chem. 30*: 405-409.
Hozumi et al. (1979). *Int. J. Cancer 123*: 119-122.
Hynes, J.B. (1970). *J. Medicinal Chem. 13*: 1235-1237.
Iwata and Hirai "Polyurethanes with Small Permanent Comressive Strain and Their Moldings." *Chemical Abstracts 125*: 28. (From *Jpn. Kokai Tokkyo Koho* JP 08,176,264 [96,176,263], 1996, Abstract No. 222822h.
Kijima et al. (1993). *J. Biol. Chem. 268*: 22429-22435.
Kim et al. (1999). *Oncogene 18*: 2461-2470.
Kwon et al. (1998). *Proc. Natl. Acad. Sci. USA 95*: 3356-3361.
Lea and Tulsyan (1995). *Anticancer Res. 15*: 879-883.
Lin et al. (1998). *Nature 391*: 811-814.
Linfield et al. (1983). *J. Med. Chem. 26*: 1741-1746.
Marks et al. (1978). *Antibiotics Chemother. 23*: 33-41.
Marks and Rifkind (1988). *Int. J. of Cell Cloning 6*: 230-240.
Marks et al. (1989). *Proc. Natl. Acad. Sci USA 86*: 6358-6362.
Melloni et al. (1988). *Proc. Natl. Acad. Sci. USA 85*: 3835-3839.
Morrison and Boyd "Conversion of Amines Into Substituted Amides." In *Organic Chemistry* (3rd ed., Allyn and Bacon, Boston, Massachusetts), pp. 755-758 (1973).
Nakajima et al. (1998). *Exp. Cell Res 241*: 126-133.
Prabhaker et al. (1985). *Arzneim.-For-sch./Drug Res. 35*: 1030-1033.
Reuben et al. (1976). *Proc. Natl. Acad.Sci. USA 173*: 862-866.
Reuben et al. (1978). *J. Biol. Chem. 253*: 4214-4218.
Reuben et al. (1980). *Biochimica et Biophysica Acta 605*: 325-346.
Richon et al. (1996). *Proc. Natl. Acad. Sci. USA 93*: 5705-5708.
Richon et al. (1998). *Proc. Natl. Acad. Sci. USA 95*: 3003-3007.
Rifkind and Marks (1978). *Blood Cells 14*: 189-206.
Saito et al. (1999). *Proc. Natl. Acad. Sci. USA 96*: 4592-4597.
Sof'ina et al. "Experimental Evaluation of Antitumor Drugs in the USA and USSR and Clinical Correlations." *National Cancer Institute Monograph 55*, Dec. 1980. NIH Publication No. 80-1933. pp. 76-78.
Tabernero et al. (1983). *1-Pharmacology 98*: 27. (From *Acta Cient. Venez*, 32: 411-416, 1981).
Tanaka et al. (1975). *Proc. Natl. Acad. Sci. USA 172*: 1003-1006.
Toi and Izumi (1961). *Chemical Abstract*, Caold Accession No. CA55:6371e.
Van Lint et al. (1996). *Gene Expression 5*: 245-253.
Weitl and Raymond (1981). *J. Org. Chem. 46*: 5234-5237.
Yoshida et al. (1990). *J. Biol. Chem. 265*: 17174-17179.

* cited by examiner

HYDROXAMIC ACID COMPOUNDS AND METHODS OF USE THEREOF

RELATED APPLICATION

This application claims the benefit of U.S. Application Ser. No. 60/459,826, filed Apr. 1, 2003, the contents of which are hereby incorporated by reference herein in their entirety.

BACKGROUND OF THE INVENTION

Compounds having a hydroxamic acid moiety have been shown to possess useful biological activities. For example, many peptidyl compounds possessing a hydroxamic acid moiety are known to inhibit matrix metalloproteinases (MMPs) which are a family of zinc endopeptidases. The MMPs play a key role in both physiological and pathological tissue degradation. Therefore, peptidyl compounds which have the ability to inhibit the action of MMPs, show utility for the treatment or prophylaxis of conditions involving tissue breakdown and inflammation. Further, compounds having a hydroxamic acid moiety have been shown to inhibit histone deacetylases (HDACs), based at least in part on the zinc binding property of the hydroxamic acid group. The inhibition of HDACs can repress gene expression, including expression of genes related to tumor suppression. Inhibition of histone deacetylase can lead to the histone-deacetylase-mediated transcriptional repression of tumor suppressor genes. For example, inhibition of histone deacetylase can provide a method for treating cancer, hematological disorders, such as hematopoiesis, and genetic related metabolic disorders.

More specifically, transcriptional regulation is a major event in cell differentiation, proliferation, and apoptosis. There are several lines of evidence that histone acetylation and deacetylation are mechanisms by which transcriptional regulation in a cell is achieved (Grunstein, M., Nature, 389: 349–52 (1997) ). These effects are thought to occur through changes in the structure of chromatin by altering the affinity of histone proteins for coiled DNA in the nucleosome. There are five types of histones that have been identified. Histones H2A, H2B, H3 and H4 are fouond in the nucleosome and H1 is a linker located between nucleosomes. Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone. This affinity causes DNA to be tightly bound to the histone and renders the DNA inaccessible to transcriptional regulatory elements and machinery. The regulation of acetylated states occurs through the balance of activity between two enzyme complexes, histone acetyl transferase (HAT) and histone deacetylase (HDAC). The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

It has been shown in several instances that the disruption of HAT or HDAC activity is implicated in the development of a malignant phenotype. For instance, in acute promyelocytic leukemia, the oncoprotein produced by the fusion of PML and RAR alpha appears to suppress specific gene transcription through the recruitment of HDACs (Lin, R. J. et al., Nature 391:811–14 (1998) ). In this manner, the neoplastic cell is unable to complete differentiation and leads to excess proliferation of the leukemic cell line.

U.S. Pat. Nos. 5,369,108, 5,932,616, 5,700,811, 6,087, 367 and 6,511,990, the contents of which are hereby incorporated by reference, disclose hydroxamic acid derivatives useful for selectively inducing terminal differentiation, cell growth arrest or apoptosis of neoplastic cells. In addition to their biological activity as antitumor agents, these hydroxamic acid derivatives have recently been identified as useful for treating or preventing a wide variety of thioredoxin (TRX)-mediated diseases and conditions, such as inflammatory diseases, allergic diseases, autoimmune diseases, diseases associated with oxidative stress or diseases characterized by cellular hyperproliferation (U.S. application Ser. No. 10/369,094, filed Feb. 15, 2003, the entire content of which is hereby incorporated by reference). Further, these hydroxamic acid derivatives have been identified as useful for treating diseases of the central nervous system (CNS) such as neurodegenerative diseases and for treating brain cancer (See, U.S. application Ser. No. 10/273,401, filed Oct. 16, 2002, the entire content of which is hereby incorporated by reference).

The inhibition of HDAC by the hydroxamic acid containing compound suberoylanilide hydroxamic acid (SAHA) disclosed in the above referenced U.S. Patents, is thought to occur through direct interaction with the catalytic site of the enzyme as demonstrated by X-ray crystallography studies (Finnin, M. S. et al., Nature 401:188–193 (1999)). The result of HDAC inhibition is not believed to have a generalized effect on the genome, but rather, only affects a small subset of the genome (Van Lint, C. et al., Gene Expression 5:245–53 (1996)). Evidence provided by DNA microarrays using malignant cell lines cultured with a HDAC inhibitor shows that there are a finite (1–2%) number of genes whose products are altered. For example, cells treated in culture with HDAC inhibitors show a consistent induction of the cyclin-dependent kinase inhibitor p21 (Archer, S. Shufen, M. Shei, A., Hodin, R. PNAS 95:6791–96 (1998)). This protein plays an important role in cell cycle arrest. HDAC inhibitors are thought to increase the rate of transcription of p21 by propagating the hyperacetylated state of histones in the region of the p21 gene, thereby making the gene accessible to transcriptional machinery. Genes whose expression is not affected by HDAC inhibitors do not display changes in the acetylation of regional associated histones (Dressel, U. et al., Anticancer Research 20(2A): 1017–22 (2000)).

Further, hydroxamic acid derivatives such as SAHA have the ability to induce tumor cell growth arrest, differentiation and/or apoptosis (Richon et al., Proc. Natl. Acad. Sci. USA, 93:5705–5708 (1996)). These compounds are targeted towards mechanisms inherent to the ability of a neoplastic cell to become malignant, as they do not appear to have toxicity in doses effective for inhibition of tumor growth in animals (Cohen, L. A. et al., Anticancer Research 19:4999–5006 (1999)).

In view of the wide variety of applications for compounds containing hydroxamic acid moieties, the development of new hydroxamic acid derivatives having improved properties, for example, increased potency or increased bioavailability is highly desirable.

SUMMARY OF THE INVENTION

The present invention relates to a novel class of hydroxamic acid derivatives. In one embodiment, the hydroxamic acid derivatives can inhibit histone deacetylase and are suitable for use in selectively inducing terminal differentiation, and arresting cell growth and/or apoptosis of neoplastic cells, thereby inhibiting proliferation of such cells. Thus, the compounds of the present are useful in treating cancer in a subject. The compounds of the invention are also useful in the prevention and treatment of TRX-mediated diseases, such as autoimmune, allergic and inflammatory diseases, and in the prevention and/or treatment of diseases of the central nervous system (CNS), such as neurodegenerative diseases.

It has been unexpectedly and surprisingly discovered that certain hydroxamic acid derivatives having at least two aryl containing groups, at least one of which is a quinolinyl, isoquinolinyl or benzyl moiety, linked to the hydroxamic acid group through a methylene chain, show improved activity as HDAC inhibitors.

The present invention relates to compounds represented by Structural Formula I and pharmaceutically acceptable salts, solvates and hydrates thereof:

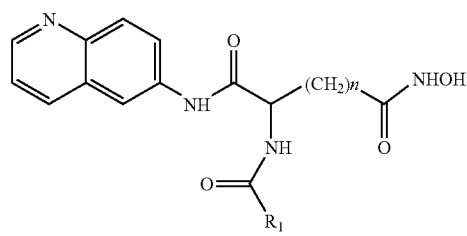

In Structural Formula I, $R_1$ is a substituted or unsubstituted aryl group, arylalkyl group, arylamino group, arylalkylamino group, aryloxy group or arylalkoxy group and n is an integer from 3 to 10.

In a particular embodiment, n is 5 for the compounds of Structural Formula I.

In another embodiment, $R_1$ is a substituted or unsubstituted heteroaryl group, phenyl group or naphthyl group for the compounds of Structural Formula I.

In yet another embodiment, $R_1$ is a substituted or unsubstituted pyridyl group, quinolinyl group or isoquinolinyl group for the compounds of Structural Formula I.

In a further embodiment, $R_1$ is a substituted or unsubstituted phenyl group for the compounds of Structural Formula I. In a particular embodiment, $R_1$ of Formula I is an unsubstituted phenyl group. In a more particular embodiment, $R_1$ of Formula I is an unsubstituted phenyl group and n is 5.

In another embodiment, $R_1$ is an unsubstituted pyridyl group for the compounds of Structural Formula I. In a particular embodiment, the unsubstituted pyridyl group is a β-pyridyl group. In a more particular embodiment, the unsubstituted pyridyl group is a β-pyridyl group and n is 5.

In yet another embodiment, $R_1$ is an unsubstituted quinolinyl group for the compounds of Structural Formula I. In a particular embodiment, the unsubstituted quinolinyl group is a 2-quinolinyl group. In a more particular embodiment, the unsubstituted quinolinyl group is a 2-quinolinyl group and n is 5.

In another embodiment, $R_1$ is a substituted or unsubstituted arylalkyloxy group for the compounds of Structural Formula I. In a particular embodiment, $R_1$ of Structural Formula I is a substituted or unsubstituted benzyloxy group. In a more particular embodiment, the benzyloxy group is and unsubstitututed benzyloxy group. In an even more particular embodiment, the benzyloxy group is an unsubstituted benzyloxy group and n is 5.

In a specific embodiment, the compound of Formula I is represented by the following structure:

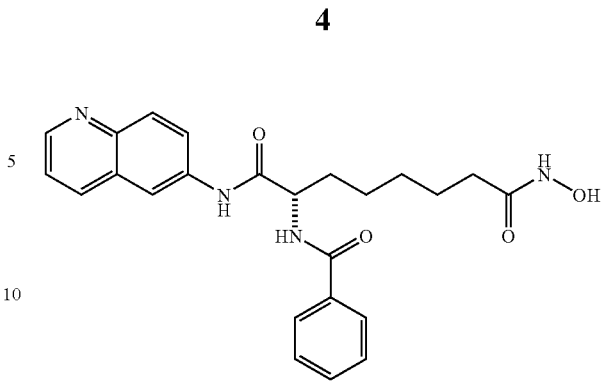

In another specific embodiment, the compound of Formula I is represented by the following structure:

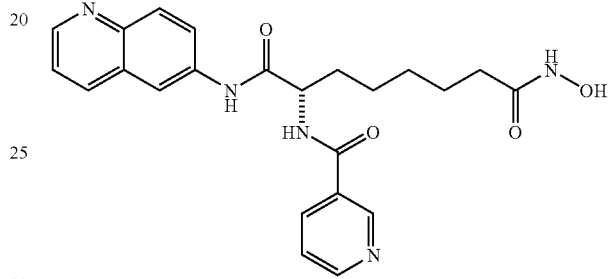

In yet another specific embodiment, the compound of Formula I is represented by the following structure:

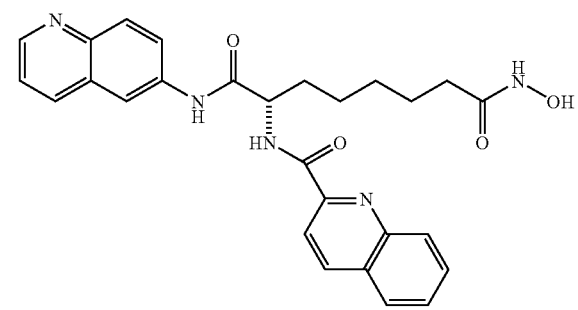

In still another specific embodiment, the compound of Formula I is represented by the following structure:

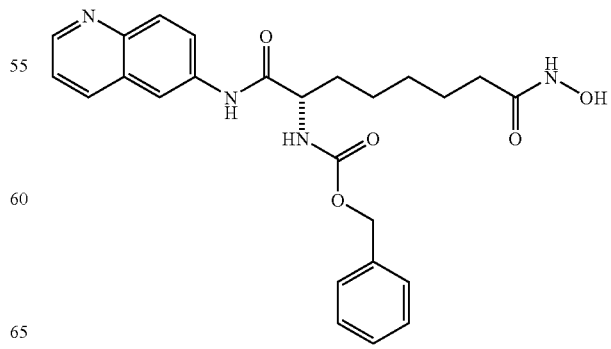

The present invention also relates to compounds of Structural Formula II and pharmaceutically acceptable salts, solvates and hydrates thereof:

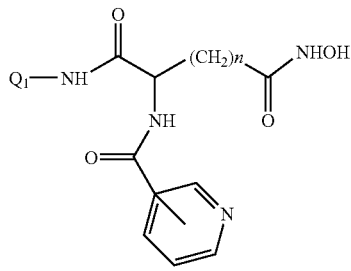

In Structural Formula II, $Q_1$ is a substituted or unsubstituted quinolinyl or isoquinolinyl group and n is an integer from 3 to 10.

In one embodiment, $Q_1$ is an 8-quinolinyl group for the compounds of Structural Formula II.

In another embodiment, the pyridyl group of Structural Formula II is a β-pyridyl group. In a particular embodiment, wherein the pyridyl group is a β-pyridyl group, $Q_1$ is an 8-quinolinyl group. In a more particular embodiment, the pyridyl group is a β-pyridyl group, $Q_1$ is an 8-quinolinyl group and n is 5.

In a specific embodiment, the compound of Formula II is represented by the following structure:

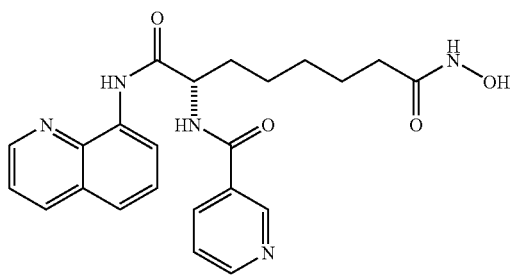

The present invention further relates to compounds of Structural Formula III and pharmaceutically acceptable salts, solvates and hydrates thereof:

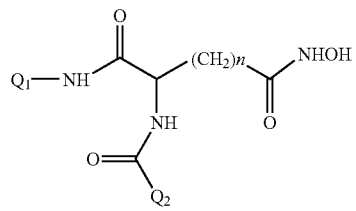

In Structural Formula III, $Q_1$ and $Q_2$ are independently a substituted or unsubstituted quinolinyl or isoquinolinyl group and n is an integer from 3 to 10.

In a particular embodiment, $Q_1$ is an 8-quinolinyl group.

In another embodiment, $Q_2$ is a 2-quinolinyl group. In a particular embodiment, wherein $Q_2$ is a 2-quinolinyl group, $Q_1$ is an 8-quinolinyl group. In a more particular embodiment, $Q_2$ is a 2-quinolinyl group, $Q_1$ is an 8-quinolinyl group and n is 5.

In a specific embodiment, the compound of Formula III is represented by the following structure:

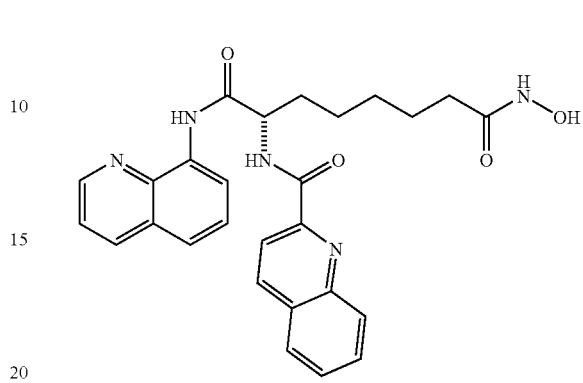

The present invention further relates to compounds of Structural Formula IV and pharmaceutically acceptable salts, solvates and hydrates thereof:

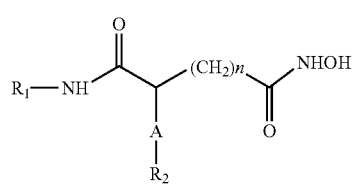

In Structural Formula IV, $R_1$ is an arylalkyl, $R_2$ is a substituted or unsubstituted aryl group, arylalkyl group, arylamino group, arylalkylamino group, aryloxy group or arylalkoxy group, A is an amide and n is an integer from 3 to 10.

In a particular embodiment, $R_1$ is a benzyl group for the compounds of Structural Formula IV.

In another embodiment, $R_1$ is a benzyl group and $R_2$ is a substituted or unsubstituted quinolinyl group for the compounds of Structural Formula IV. In a particular embodiment, $R_2$ is an unsubstituted quinolinyl group. In an even more particular embodiment, the unsubstituted quinolinyl group is a 2-quinolinyl group. In a further embodiment, $R_1$ is a benzyl group, $R_2$ is a 2-quinolinyl group and n is 5.

In a specific embodiment, the compound of Formula IV is represented by the following structure:

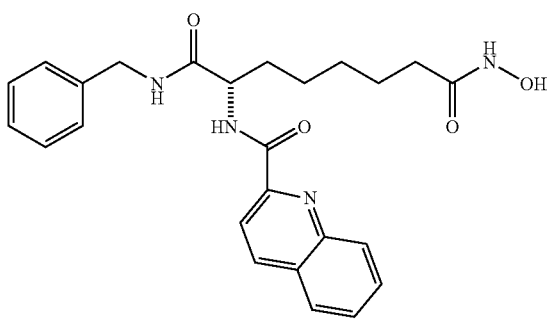

In yet another embodiment, $R_1$ is a benzyl group and $R_2$ is a substituted or unsubstituted benzyloxy group for the compounds of Structural Formula IV. In a particular embodiment, $R_2$ is an unsubstituted benzyloxy group. In a further embodiment, $R_1$ is a benzyl group, $R_2$ is an unsubstituted benzyloxy group and n is 5.

In a specific embodiment, the compound of Formula IV is represented by the following structure:

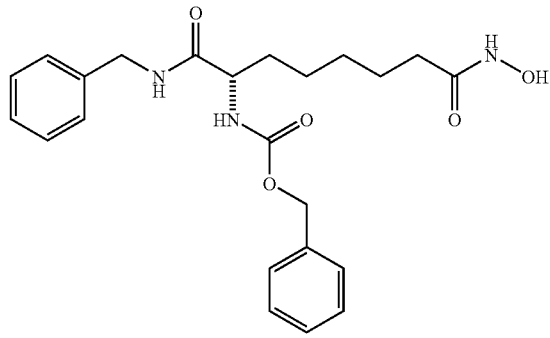

In still another embodiment, $R_1$ is a benzyl group and $R_2$ is a substituted or unsubstituted phenyl group for the compounds of Structural Formula IV. In a particular embodiment, $R_2$ is an unsubstituted phenyl group. In a further embodiment, $R_1$ is a benzyl group, $R_2$ is an unsubstituted phenyl group and n is 5.

In a specific embodiment, the compound of Formula IV is represented by the following structure:

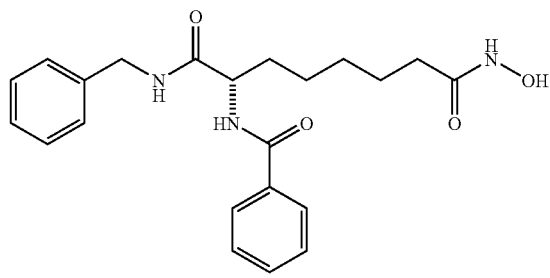

In another embodiment, $R_1$ is a benzyl group and $R_2$ is a substituted or unsubstituted pyridyl group for the compounds of Structural Formula IV. In a particular embodiment, $R_2$ is an unsubstituted pyridyl group. In an even more particular embodiment, the unsubstituted pyridyl group is a β-pyridyl. In a further embodiment, $R_1$ is a benzyl group, $R_2$ is a β-pyridyl group and n is 5.

In a specific embodiment, the compound of Formula IV is represented by the following structure:

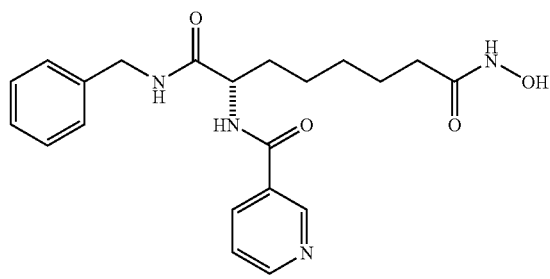

The invention also relates to a pharmaceutical composition comprising a therapeutically effective amount of any one of the hydroxamic acid compounds and a pharmaceutically acceptable carrier.

The invention further relates to use of the hydroxamic acid compounds for the manufacture of a medicament for treating the diseases and disorders described herein such as cancer, TRX-mediated diseases and disorders and neurodegenerative diseases and disorders.

The invention also relates to method of using the hydroxamic acid derivatives described herein.

In a particular embodiment, the invention relates to a method of treating cancer in a subject in need of treatment comprising administering to said subject a therapeutically effective amount of a hydroxamic acid derivative described herein.

In another embodiment, the method of use is a method of selectively inducing terminal differentiation of neoplastic cells and thereby inhibiting proliferation of such cells. The method comprises contacting the cells under suitable conditions with an effective amount of one or more of the hydroxamic acid compounds described herein.

In another embodiment, the hydroxamic acid derivatives are used in a method of selectively inducing cell growth arrest of neoplastic cells and thereby inhibiting proliferation of such cells. The method comprises contacting the cells under suitable conditions with an effective amount of one or more of the hydroxamic acid compounds described herein.

In yet another embodiment, the hydroxamic acid derivatives are used in a method of inducing terminal differentiation of tumor cells in a tumor comprising contacting the cells with an effective amount of any one or more of the hydroxamic acid compounds described herein.

In still another embodiment, the hydroxamic acid derivatives are used in a method of inhibiting the activity of histone deacetylase comprising contacting the histone deacetylase with an effective amount of one or more of the hydroxamic acid compounds described herein.

In another embodiment, the hydroxamic acid derivatives are used in a method of treating a thioredoxin (TRX)-mediated disease or disorder in a subject in need thereof, comprising administering to the subject a therapeutically effective amount of one or more of the hydroxamic acid compounds described herein.

In another embodiment, the hydroxamic acid derivatives are used in a method of treating a disease of the central nervous system in a subject in need thereof comprising administering to the subject a therapeutically effective amount of any one or more of the hydroxamic acid compounds.

In particular embodiments, the CNS disease is a neurodegenerative disease. In further embodiments, the neurogenerative disease is an inherited neurodegenerative disease, such as those inherited neurodegenerative diseases which are polyglutamine expansion diseases.

The invention further relates to use of the compounds described herein for the manufacture of a medicament for treating cancer (e.g., brain cancer) and for treating thioredoxin (TRX)-mediated diseases.

The foregoing and other objects, features and advantages of the invention will be apparent from the following more particular description of preferred embodiments of the invention.

DETAILED DESCRIPTION OF THE INVENTION

A description of preferred embodiments of the invention follows.

The present invention relates to a novel class of hydroxamic acid derivatives. In one embodiment, the hydroxamic acid derivatives can inhibit histone deacetylase and are suitable for use in selectively inducing terminal differentiation, and arresting cell growth and/or apoptosis of neoplastic cells, thereby inhibiting proliferation of such cells. Thus, the compounds of the present are useful in treating cancer a subject. The compounds of the invention are also useful in the prevention and treatment of TRX-mediated diseases, such as autoimmune, allergic and inflammatory diseases, and in the prevention and/or treatment of diseases of the central nervous system (CNS), such as neurodegenerative diseases.

It has been unexpectedly and surprisingly discovered that certain hydroxamic acid derivatives having at least two aryl containing groups, at least one of which is a quinolinyl, isoquinolinyl or benzyl moiety, linked to the hydroxamic acid group through a methylene chain, show improved activity as HDAC inhibitors.

Compounds

The present invention relates to compounds represented by Structural Formula I and pharmaceutically acceptable salts, solvates and hydrates thereof:

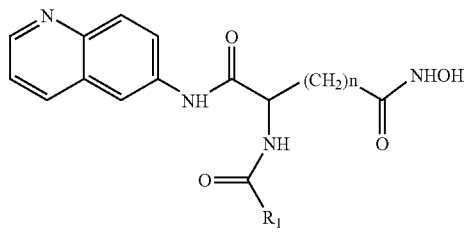

I

In Structural Formula I, $R_1$ is a substituted or unsubstituted aryl group, arylalkyl group, arylamino group, arylalkylamino group, aryloxy group or arylalkoxy group and n is an integer from 3 to 10.

In a particular embodiment, n is 5 for the compounds of Structural Formula I.

In another embodiment, $R_1$ is a substituted or unsubstituted heteroaryl group, phenyl group or naphthyl group for the compounds of Structural Formula I.

In yet another embodiment, $R_1$ is a substituted or unsubstituted pyridyl group, quinolinyl group or isoquinolinyl group for the compounds of Structural Formula I.

In a further embodiment, $R_1$ is a substituted or unsubstituted phenyl group for the compounds of Structural Formula I. In a particular embodiment, $R_1$ of Formula I is an unsubstituted phenyl group. In a more particular embodiment, $R_1$ of Formula I is an unsubstituted phenyl group and n is 5.

In another embodiment, $R_1$ is an unsubstituted pyridyl group for the compounds of Structural Formula I. In a particular embodiment, the unsubstituted pyridyl group is a β-pyridyl group. In a more particular embodiment, the unsubstituted pyridyl group is a β-pyridyl group and n is 5.

In yet another embodiment, $R_1$ is an unsubstituted quinolinyl group for the compounds of Structural Formula I. In a particular embodiment, the unsubstituted quinolinyl group is a 2-quinolinyl group. In a more particular embodiment, the unsubstituted quinolinyl group is a 2-quinolinyl group and n is 5.

In another embodiment, $R_1$ is a substituted or unsubstituted arylalkyloxy group for the compounds of Structural Formula I. In a particular embodiment, $R_1$ of Structural Formula I is a substituted or unsubstituted benzyloxy group. In a more particular embodiment, the benzyloxy group is and unsubstitututed benzyloxy group. In an even more particular embodiment, the benzyloxy group is an unsubstituted benzyloxy group and n is 5.

In a specific embodiment, the compound of Formula I is represented by the following structure:

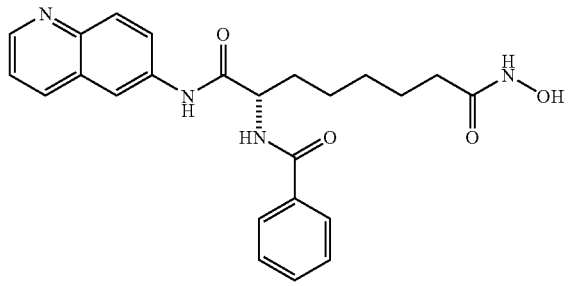

In another specific embodiment, the compound of Formula I is represented by the following structure:

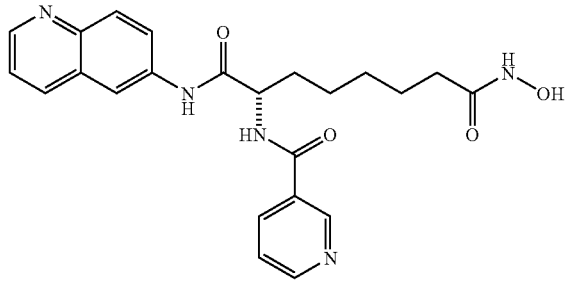

In yet another specific embodiment, the compound of Formula I is represented by the following structure:

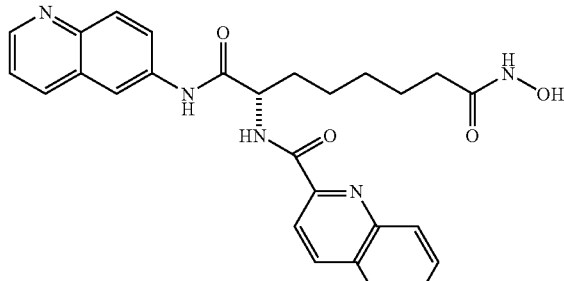

In still another specific embodiment, the compound of Formula I is represented by the following structure:

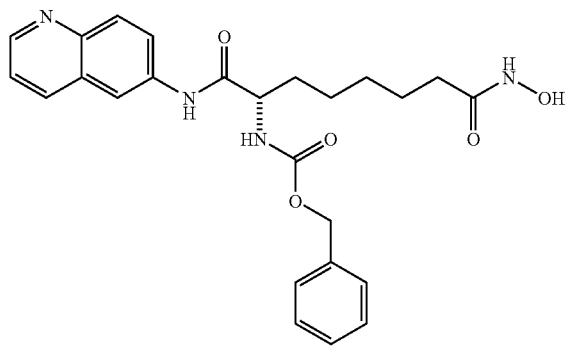

The present invention also relates to compounds of Structural Formula II and pharmaceutically acceptable salts, solvates and hydrates thereof:

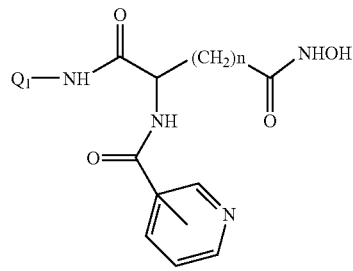

In Structural Formula II, $Q_1$ is a substituted or unsubstituted quinolinyl or isoquinolinyl group and n is an integer from 3 to 10.

In one embodiment, $Q_1$ is an 8-quinolinyl group for the compounds of Structural Formula II.

In another embodiment, the pyridyl group of Structural Formula II is a β-pyridyl group. In a particular embodiment, wherein the pyridyl group is a β-pyridyl group, $Q_1$ is an 8-quinolinyl group. In a more particular embodiment, the pyridyl group is a β-pyridyl group, $Q_1$ is an 8-quinolinyl group and n is 5.

In a specific embodiment, the compound of Formula II is represented by the following structure:

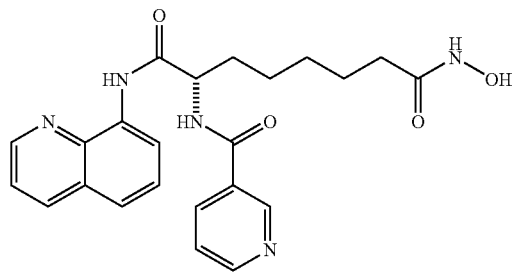

The present invention further relates to compounds of Structural Formula III and pharmaceutically acceptable salts, solvates and hydrates thereof:

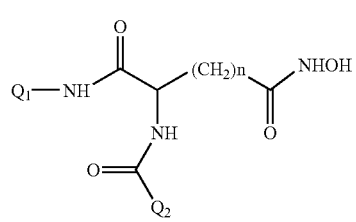

In Structural Formula III, $Q_1$ and $Q_2$ are independently a substituted or unsubstituted quinolinyl or isoquinolinyl group and n is an integer from 3 to 10.

In a particular embodiment, $Q_1$ is an 8-quinolinyl group.

In another embodiment, $Q_2$ is a 2-quinolinyl group. In a particular embodiment, wherein $Q_2$ is a 2-quinolinyl group, $Q_1$ is an 8-quinolinyl group. In a more particular embodiment, $Q_2$ is a 2-quinolinyl group, $Q_1$ is an 8-quinolinyl group and n is 5.

In a specific embodiment, the compound of Formula III is represented by the following structure:

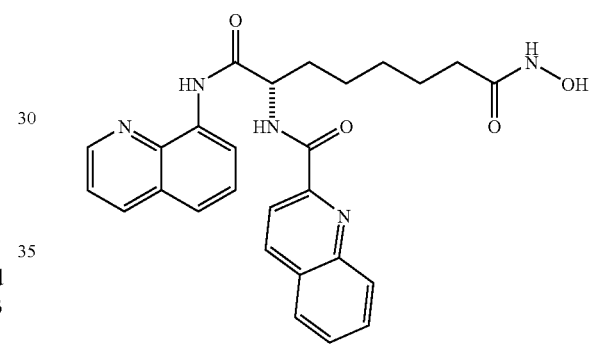

The present invention further relates to compounds of Structural Formula IV and pharmaceutically acceptable salts, solvates and hydrates thereof:

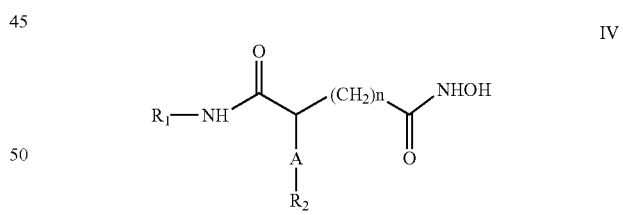

In Structural Formula IV, $R_1$ is an arylalkyl, $R_2$ is a substituted or unsubstituted aryl group, arylalkyl group, arylamino group, arylalkylamino group, aryloxy group or arylalkoxy group, A is an amide and n is an integer from 3 to 10.

In a particular embodiment, $R_1$ is a benzyl group for the compounds of Structural Formula IV.

In another embodiment, $R_1$ is a benzyl group and $R_2$ is a substituted or unsubstituted quinolinyl group for the compounds of Structural Formula IV. In a particular embodiment, $R_2$ is an unsubstituted quinolinyl group. In an even more particular embodiment, the unsubstituted quinolinyl group is a 2-quinolinyl group. In a further embodiment, $R_1$ is a benzyl group, $R_2$ is a 2-quinolinyl group and n is 5.

In a specific embodiment, the compound of Formula IV is represented by the following structure:

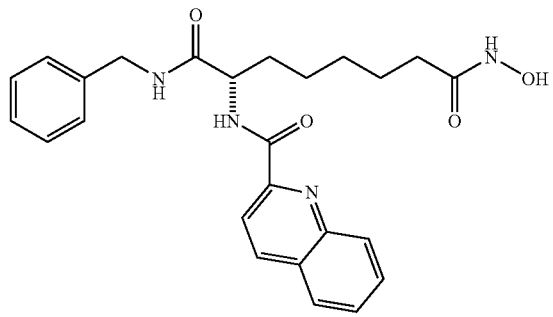

In yet another embodiment, $R_1$ is a benzyl group and $R_2$ is a substituted or unsubstituted benzyloxy group for the compounds of Structural Formula IV. In a particular embodiment, $R_2$ is an unsubstituted benzyloxy group. In a further embodiment, $R_1$ is a benzyl group, $R_2$ is an unsubstituted benzyloxy group and n is 5.

In a specific embodiment, the compound of Formula IV is represented by the following structure:

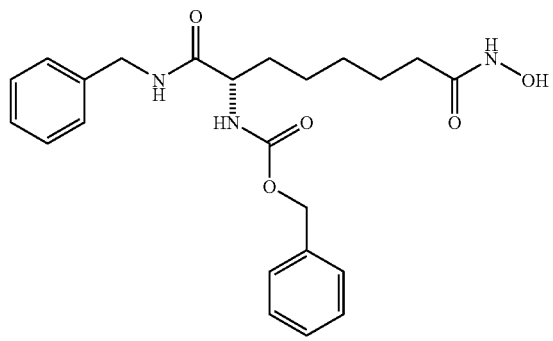

In still another embodiment, $R_1$ is a benzyl group and $R_2$ is a substituted or unsubstituted phenyl group for the compounds of Structural Formula IV. In a particular embodiment, $R_2$ is an unsubstituted phenyl group. In a further embodiment, $R_1$ is a benzyl group, $R_2$ is an unsubstituted phenyl group and n is 5.

In a specific embodiment, the compound of Formula IV is represented by the following structure:

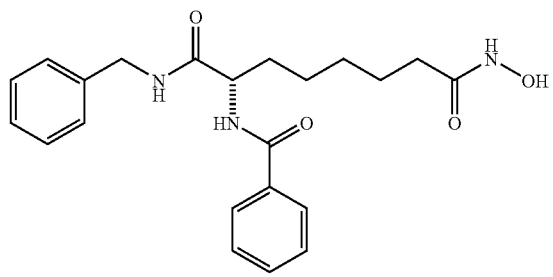

In another embodiment, $R_1$ is a benzyl group and $R_2$ is a substituted or unsubstituted pyridyl group for the compounds of Structural Formula IV. In a particular embodiment, $R_2$ is an unsubstituted pyridyl group. In an even more particular embodiment, the unsubstituted pyridyl group is a β-pyridyl. In a further embodiment, $R_1$ is a benzyl group, $R_2$ is a β-pyridyl group and n is 5.

In a specific embodiment, the compound of Formula IV is represented by the following structure:

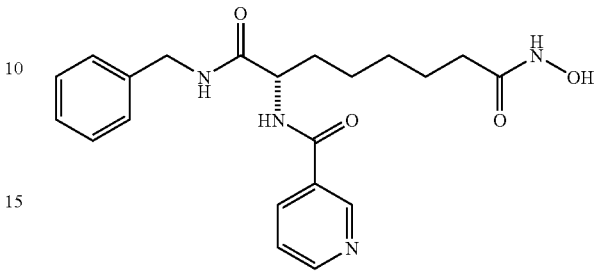

The invention also relates to a pharmaceutical composition comprising a therapeutically effective amount of any one of the hydroxamic acid compounds and a pharmaceutically acceptable carrier.

An "aliphatic group" is non-aromatic, consists solely of carbon and hydrogen and can optionally contain one or more units of unsaturation, e.g., double and/or triple bonds. An aliphatic group can be straight chained, branched or cyclic. When straight chained or branched, an aliphatic group typically contains between about 1 and about 12 carbon atoms, more typically between about 1 and about 6 carbon atoms. When cyclic, an aliphatic group typically contains between about 3 and about 10 carbon atoms, more typically between about 3 and about 7 carbon atoms. Aliphatic groups are preferably $C_1$–$C_{12}$ straight chained or branched alkyl groups (i.e., completely saturated aliphatic groups), more preferably $C_1$–$C_6$ straight chained or branched alkyl groups. Examples include methyl, ethyl, n-propyl, iso-propyl, n-butyl, sec-butyl and tert-butyl.

An "aromatic group" (also referred to as an "aryl group") as used herein includes carbocyclic aromatic groups, heterocyclic aromatic groups (also referred to as "heteroaryl") and fused polycyclic aromatic ring system as defined herein.

A "carbocyclic aromatic group" is an aromatic ring of 5 to 14 carbons atoms, and includes a carbocyclic aromatic group fused with a 5-or 6-membered cycloalkyl group such as indan. Examples of carbocyclic aromatic groups include, but are not limited to, phenyl, naphthyl, e.g., 1-naphthyl and 2-naphthyl; anthracenyl, e.g., 1-anthracenyl, 2-anthracenyl; phenanthrenyl; fluorenonyl, e.g., 9-fluorenonyl, indanyl and the like. A carbocyclic aromatic group is optionally substituted with a designated number of substituents, described below.

A "heterocyclic aromatic group" (or "heteroaryl") is a monocyclic, bicyclic or tricyclic aromatic ring of 5- to 14-ring atoms of carbon and from one to four heteroatoms selected from O, N, or S. Examples of heteroaryl include, but are not limited to pyridyl, e.g., 2-pyridyl (also referred to as α-pyridyl), 3-pyridyl (also referred to as β-pyridyl) and 4-pyridyl (also referred to as γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazoyl, 4-oxazoyl and 5-oxazoyl; isoxazoyl; pyrrolyl; pyridazinyl; pyrazinyl and the like. Heterocyclic aromatic (or heteroaryl) as defined above may be optionally substituted with a designated number of substituents, as described below for aromatic groups.

A "fused polycyclic aromatic" ring system is a carbocyclic aromatic group or heteroaryl fused with one or more other heteroaryl or nonaromatic heterocyclic ring. Examples include, quinolinyl and isoquinolinyl, e.g, 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl e.g., 2-benzofuranyl and 3-benzofuranyl; dibenzofuranyl.e.g., 2,3-dihydrobenzofuranyl; dibenzothiophenyl; benzothienyl, e.g., 2-benzothienyl and 3-benzothienyl; indolyl, e.g., 2-indolyl and 3-indolyl; benzothiazolyl, e.g., 2-benzothiazolyl; benzooxazolyl, e.g., 2-benzooxazolyl; benzimidazolyl, e.g., 2-benzoimidazolyl; isoindolyl, e.g., 1-isoindolyl and 3-isoindolyl; benzotriazolyl; purinyl; thianaphthenyl and the like. Fused polycyclic aromatic ring systems may optionally be substituted with a designated number of substituents, as described herein.

An "aralkyl group" (arylalkyl) is an alkyl group substituted with an aromatic group, preferably a phenyl group. A preferred aralkyl group is a benzyl group. Suitable aromatic groups are described herein and suitable alkyl groups are described herein. Suitable substituents for an aralkyl group are described herein.

An "aryloxy group" is an aryl group that is attached to a compound via an oxygen (e.g., phenoxy).

An "alkoxy group, as used herein, is a straight chain or branched c1–c12 or cyclic $C_3$–$C_{12}$ alkyl group that is connected to a comound via an oxygen atom. Examples of alkoxy groups include but are not limited to methoxy, ethoxy and propoxy.

An "arylalkoxy group" is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

As used herein, an "arylalkylamino group" is an arylalkyl group that is attached to a compound via a nitrogen on the alkyl portion of the arylalkyl.

As used herein, many moieties or groups are referred to as being either "substituted or unsubstituted". When a moiety is referred to as substituted, it denotes that any portion of the moiety that is known to one skilled in the art as being available for substitution can be substituted. For example, the substitutable group can be a hydrogen atom which is replaced with a group other than hydrogen (i.e., a substituent group). Multiple substituent groups can be present. When multiple substituents are present, the substituents can be the same or different and substitution can be at any of the substitutable sites on the ring. Such means for substitution are well-known in the art. For purposes of exemplification, which should not be construed as limiting the scope of this invention, some examples of groups that are substituents are: alkyl groups (which can also be substituted, such as $CF_3$), alkoxy groups (which can be substituted, such as $OCF_3$), a halogen or halo group (F, Cl, Br, I), hydroxy, nitro, oxo, —CN, —COH, —COOH, amino, N-alkylamino or N,N-dialkylamino (in which the alkyl groups can also be substituted), esters (—C(O)—OR, where R can be a group such as alkyl, aryl, etc., which can be substituted), aryl (most preferred is phenyl, which can be substituted) and arylalkyl (which can be substituted).

The hydroxamic acid derivatives described herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and ferric salts as well as salts with organic bases such as isopropylamine, trimethylamine, 2-ethylamino ethanol, histidine, procaine, dicyclohexylamine and N-methyl-D-glucamine.

The active compounds disclosed can, as noted above, be prepared in the form of their hydrates, such as hemihydrate, monohydrate, dihydrate, trihydrate, tetrahydrate and the like and as solvates.

Stereochemistry

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture.

Many of the compounds described herein can have one or more chiral centers and therefore can exist in different enantiomeric forms. If desired, a chiral carbon can be designated with an asterisk (*). When bonds to the chiral carbon are depicted as straight lines in the formulas of the invention, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When compounds of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, for example by formation of diastereoisomeric salts which may be separated, for example, by crystallization (See, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. For example, the enantiomeric excess can be about 60% or more, such as about 70% or more, for example about 80% or more, such as about 90% or more. In a particular embodiment when a specific absolute configuration is designated, the enantiomeric excess of depicted compounds is at least about 90%. In a more particular embodiment, the enantiomeric excess of the compounds is at least about 95%, such as at least about 97.5%, for example, at least 99% enantiomeric excess.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R) are mirror image stereoisomers of one another. The stereoisomers which are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

As used herein, "a," an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes includes mixtures of two or more carriers as well as a single carrier, and the like.

Method of Treatment

The invention also relates to methods of using the hydroxamic acid derivatives described herein.

In one embodiment, the invention relates to a method of treating cancer in a subject in need of treatment comprising administering to said subject a therapeutically effective amount of a hydroxamic acid compound described herein.

As used herein, cancer refers to tumors, neoplasms, carcinomas, sarcomas, leukemias, lymphomas and the like.

For example, cancers include, but are not limited to, leukemias and lymphomas such as cutaneous T-cell lymphoma (CTCL), non-cutaneous peripheral T-cell lymphoma, lymphomas associated with human T-cell lymphotropic virus (HTLV), for example, adult T-cell leukemia/lymphoma (ATLL), acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms Tumor, bone tumors, and soft-tissue sarcomas, common solid tumors of adults such as head and neck cancers (e.g., oral, laryngeal and sophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

In another embodiment, the method of use is a method of selectively inducing terminal differentiation of neoplastic cells and thereby inhibiting proliferation of such cells. The method comprises contacting the cells under suitable conditions with an effective amount of a hydroxamic acid compound described herein.

In another embodiment, the hydroxamic acid derivatives are used in a method of selectively inducing cell growth arrest of neoplastic cells and thereby inhibiting proliferation of such cells. The method comprises contacting the cells under suitable conditions with an effective amount of a hydroxamic acid compound described herein.

In yet another embodiment, the hydroxamic acid derivatives are used in a method of inducing terminal differentiation of tumor cells in a tumor comprising contacting the cells with an effective amount of a hydroxamic acid compounds described herein.

In still another embodiment, the hydroxamic acid derivatives are used in a method of inhibiting the activity of histone deacetylase comprising contacting the histone deacetylase with an effective amount of one or more of the hydroxamic acid compouonds described herein.

In another embodiment, the hydroxamic acid derivatives are used in a method of treating a thioredoxin (TRX)-mediated disease or disorder in a subject in need thereof, comprising administering to the subject a therapeutically effective amount of one or more of the hydroxamic acid compounds described herein.

Examples of TRX-mediated diseases include, but are not limited to, acute and chronic inflammatory diseases, autoimmune diseases, allergic diseases, diseases associated with oxidative stress, and diseases characterized by cellular hyperproliferation.

Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation),; hemohorragic shock; hyperalgesia: inflammatory bowel disease; multiple sclerosis; myopathies (e.g., muscle protein metabolism, esp. in sepsis); osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes. Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

In another embodiment, the hydroxamic acid derivatives are used in a method of treating a disease of the central nervous system in a subject in need thereof comprising administering to the subject a therapeutically effective amount of any one or more of the hydroxamic acid compounds described herein.

In a particular embodiment, the CNS disease is a neurodegenerative disease. In a further embodiment, the neurogenerative disease is an inherited neurodegenerative disease, such as those inherited neurodegenerative diseases which are polyglutamine expansion diseases.

Generally, neurodegenerative diseases can be grouped as follows:

I. Disorders characterized by progressive dementia in the absence of other prominent neurologic signs.
   A. Alzheimer's disease
   B. Senile dementia of the Alzheimer type
   C. Pick's disease (lobar atrophy)
II. Syndromes combining progressive dementia with other prominent neurologic abnormalities
   A. Mainly in adults
      1. Huntington's disease
      2. Multiple system atrophy combining dementia with ataxia and/or manifestations of Parkinson's disease
      3. Progressive supranuclear aplsy (Steel-Richardson-Olszewski)
      4. Diffuse Lewy body disease
      5. Corticodentatonigral degeneration
   B. Mainly in children or young adults
      1. Hallervorden-Spatz disease
      2. Progressive familial myoclonic epilepsy
III. Syndromes of gradually developing abnormalities of posture and movement
   A. Paralysis agitans (Parkinson's disease)
   B. Striatonigral degeneration
   C. Progressive supranuclear palsy
   D. Torsion dystonia (torsion spasm; dystonia musculorum deformans)
   E. Spasmodic torticollis and other dyskinesis
   F. Familial tremor
   G. Gilles de la Tourette syndrome
IV. Syndromes of progressive ataxia
   A. Cerebellar degenerations
      1. Cerebellar cortical degeneration
      2. Olivopontocerebellar atrophy (OPCA)
   B. Spinocerebellar degeneration (Friedreich's atazia and related disorders)
V. Syndrome of central autonomic nervous system failure (Shy-Drager syndrome)
VI. Syndromes of muscular weakness and wasting without sensory changes (motor neuron disease)
   A. Amyotrophic lateral sclerosis
   B. Spinal muscular atrophy
      1. Infantile spinal muscular atrophy (Werdnig-Hoffman)
      2. Juvenile spinal muscular atrophy (Wohlfart-Kugelberg-Welander)
      3. Other forms of familial spinal muscular atrophy
   C. Primary lateral sclerosis
   D. Hereditary spastic paraplegia
VII. Syndromes combining muscular weakness and wasting with sensory changes (progressive neural muscular atrophy; chronic familial polyneuropathies)
   A. Peroneal muscular atrophy (Charcot-Marie-Tooth)
   B. Hypertrophic interstitial polyneuropathy (Dejerine-Sottas)
   C. Miscellaneous forms of chronic progressive neuropathy
VIII Syndromes of progressive visual loss
   A. Pigmentary degeneration of the retina (retinitis pigmentosa)
   B. Hereditary optic atrophy (Leber's disease)

As used herein, therapeutically effective or effective amount refers to an amount which elicits the desired therapeutic or biological effect. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

For example, when the method is a method of treating cancer, a therapeutically effective amount can be an amount which is inhibits (partially or totally) the formation of a tumor or a hematological malignancy, reverses the development of a tumor or other malignancy, prevents or reduces its further progression, prevents its development (chemopreventive) or treats cancer metastases.

Further, a therapeutically effective amount, can be an amount which selectively induces terminal differentiation of neoplastic cells, an amount which selectively induces cell growth arrest of neoplastic cells or an amount that induces terminal differentiation of tumor cells.

When the method is a method for treating and/or preventing thioredoxin (TRX)-mediated diseases and conditions, a therapeutically effective amount is an amount which regulates, for example, increases, decreases or maintains a physiologically suitable level of TRX in the subject in need of treatment to elicit the desired therapeutic effect. The therapeutic effect is dependent upon the specific TRX-mediated disease or condition being treated. As such, the therapeutic effect can be a decrease in the severity of symptoms associated with the disease or disorder and/or inhibition (partial or complete) of progression of the disease or disease.

In addition, a therapeutically effective amount can be an amount which inhibits histone deacetylase.

Subject, as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

Pharmaceutical Compositions

The compounds of the invention, and derivatives, fragments, analogs, homologs pharmaceutically acceptable salts, hydrates or solvates thereof, can be incorporated into pharmaceutical compositions suitable for various modes of administration, together with a pharmaceutically acceptable carrier or excipient. Such compositions typically comprise a therapeutically effective amount of any of the compounds above, and a pharmaceutically acceptable carrier.

The hydroxamic acid derivatives can be administered in such oral forms as tablets, capsules (each of which includes sustained release or timed release formulations), pills, powders, granules, elixers, tinctures, suspensions, syrups, and emulsions. Likewise, the hydroxamic acid derivatives can be administered in intravenous (bolus or infusion), intraperitoneal, subcutaneous, or intramuscular form, all using forms well known to those of ordinary skill in the pharmaceutical arts.

Routes of administration also include any other conventional and physiologically acceptable route, such as, for example, inhalation (via a fine powder formulation or a fine mist), transdermal, nasal, vaginal, rectal, or sublingual routes of administration and can be formulated in dosage forms appropriate for each route of administration.

The hydroxamic acid derivatives of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The hydroxamic acid derivatives can also be delivered by the use of monoclonal antibodies as individual carriers to which the compound molecules are coupled. The hydroxamic acid derivatives can also be prepared with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the Hydroxamic acid derivatives can be prepared with biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The hydroxamic acid derivatives can be administered as active ingredients in admixture with suitable pharmaceutical diluents, excipients or carriers (collectively referred to herein as "carrier" materials) suitably selected with respect to the intended form of administration, and consistent with conventional pharmaceutical practices.

For instance, for oral administration in the form of a tablet or capsule, the hydroxamic acid derivative can be combined with an oral, non-toxic, pharmaceutically acceptable, inert carrier. Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In addition, buffers (e.g.,) of various pH and ionic strength can be used in the formulations. Tris-HCl., Phosphate Glucuronic acid, L-lactic acid, acetic acid, citric acid or any pharmaceutically acceptable acid/conjugate base with reasonable buffering capacity in the pH range acceptable for intravenous administration of the hydroxamic acid derivative can be used as buffers. Sodium chloride solution wherein the pH has been adjusted to the desired range with either acid or base, for example, hydrochloric acid or sodium hydroxide, can also be employed. Typically, a pH range for the intravenous formulation can be in the range of from about 5 to about 12. A preferred pH range for intravenous formulation wherein can be about 9 to about 12. Consideration should be given to the solubility and chemical compatibility of the compound in choosing an appropriate excipient.

Subcutaneous formulations, preferably prepared according to procedures well known in the art at a pH in the range between about 5 and about 12, also include suitable buffers and isotonicity agents. They can be formulated to deliver a daily dose of the active compound in one or more daily subcutaneous administrations, e.g., one, two or three times each day. The choice of appropriate buffer and pH of a formulation, depending on solubility of the hydroxamic acid derivative to be administered, is readily made by a person having ordinary skill in the art. Sodium chloride solution wherein the pH has been adjusted to the desired range with either acid or base, for example, hydrochloric acid or sodium hydroxide, can also be employed in the subcutaneous formulation. Typically, a pH range for the subcutaneous formulation can be in the range of from about 5 to about 12. A preferred pH range for subcutaneous formulation can be about 9 to about 12. Consideration should be given to the solubility and chemical compatibility of the hydroxamic acid derivative in choosing an appropriate excipient.

The hydroxamic acid derivatives can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

In the treatment of rheumatoid arthritis the hydroxamic acid derivative can be administered directly into the synovial fluid and/or synovial tissue of the rheumatic joint such that a local effect of the inhibitor is realized.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

Dosing

The dosage regimen utilizing the compounds of the present invention can be selected in accordance with a variety of factors including type, species, age, weight, sex and the disease being treated; the severity of the condition to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

Oral dosages of the hydroxamic acid derivatives, when used to treat the desired disease, can range between about 2 mg to about 2000 mg per day, such as from about 20 mg to about 2000 mg per day, such as from about 200 mg to about 2000 mg per day. For example, oral dosages can be about 2, about 20, about 200, about 400, about 800, about 1200, about 1600 or about 2000 mg per day. It is understood that the total amount per day can be administered in a single dose or can be administered in multiple dosings such as twice, three or four times per day.

For example, a patient can receive between about 2 mg/day to about 2000 mg/day, for example, from about 20–2000 mg/day, such as from about 200 to about 2000 mg/day, for example from about 400 mg/day to about 1200 mg/day. A suitably prepared medicament for once a day administration can thus contain between about 2 mg and about 2000 mg, such as from about 20 mg to about 2000 mg, such as from about 200 mg to about 1200 mg, such as from about 400 mg/day to about 1200 mg/day. The Hydroxamic acid derivatives can be administered in a single dose or in divided doses of two, three, or four times daily. For administration twice a day, a suitably prepared medicament would therefore contain half of the needed daily dose.

Intravenously or subcutaneously, the patient would receive the hydroxamic acid derivative in quantities sufficient to deliver between about 3–1500 mg/m$^2$ per day, for example, about 3, 30, 60, 90, 180, 300, 600, 900, 1200 or 1500 mg/m$^2$ per day. Such quantities may be administered in a number of suitable ways, e.g. large volumes of low concentrations of Hydroxamic acid derivative during one extended period of time or several times a day. The quantities can be administered for one or more consecutive days, intermittent days or a combination thereof per week (7 day period). Alternatively, low volumes of high concentrations of the hydroxamic acid derivative during a short period of time, e.g. once a day for one or more days either consecutively, intermittently or a combination thereof per week (7 day period). For example, a dose of 300 mg/m$^2$ per day can be administered for consecutive days for a total of 1500 mg/m$^2$ per treatment. In another dosing regimen, the number of consecutive days can also be, with treatment lasting for 2 or 3 consecutive weeks for a total of 3000 mg/m2 and 4500 mg/m$^2$ total treatment.

Typically, an intravenous formulation may be prepared which contains a concentration of a hydroxamic acid derivative of between about 1.0 mg/mL to about 10 mg/mL, e.g. 2.0 mg/mL, 3.0 mg/mL, 4.0 mg/mL, 5.0 mg/mL, 6.0 mg/mL, 7.0 mg/mL, 8.0 mg/mL, 9.0 mg/mL and 10 mg/mL and administered in amounts to achieve the doses described above. In one example, a sufficient volume of intravenous formulation can be administered to a patient in a day such that the total dose for the day is between about 300 and about 1500 mg/m2.

Combination Therapy

The hydroxamic acid compounds of the present invention can be administered alone or in combination with other therapies suitable for the disease or disorder being treated.

Where separate dosage formulations are used, the hydroxamic acid compound and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the hydroxamic acid compound and the other therapeutic agent are realized by the patient at substantially the same time. Such beneficial effect is preferably achieved when the target blood level concentrations of each active drug are maintained at substantially the same time.

In one embodiment, the present invention provides the hydroxamic acid compounds described herein in combination with an antitumor agent, a hormone, a steroid, or a retinoid.

A suitable antitumor agent can be one of numerous chemotherapy agents such as an alkylating agent, an antimetabolite, a hormonal agent, an antibiotic, colchicine, a vinca alkaloid, L-asparaginase, procarbazine, hydroxyurea, mitotane, nitrosoureas or an imidazole carboxamide. Suitable agents are those agents which promote depolarization of tubulin. Preferably the antitumor agent is colchicine or a vinca alkaloid; especially preferred are vinblastine and vincristine.

Experimental

EXAMPLE 1

Synthesis

The compounds of the present invention were prepared by the general method outlined in the synthetic schemes below, as exemplified below for Compounds 1 and 6.

TABLE 1

| Compound No. | Ar$_1$ | Ar$_2$ | MW |
|---|---|---|---|
| 1 | 6-quinolinyl | O(CH2)Ph | 464.5 |
| 6 | 6-quinolinyl | Phenyl | 434.5 |

COMPOUND DESCRIPTION

Briefly, the generation of the amino-suberates started with commercially available doubly-protected amino-suberate (Scheme 1). The dicyclohexylamine salt was removed with aqueous hydrogen chloride to yield the free acid. Typical amide coupling yielded the Cbz-protected amine, which was deprotected and acylated to the diester. The hydrogenolysis was bypassed for 6a, since the final product contained the Cbz moiety. The acids were protected with TFA in CH$_2$Cl$_2$, and the final hydroxamic acid formation was achieved via mixed anhydride formation and quenching with hydroxylamine.

SCHEME 1:

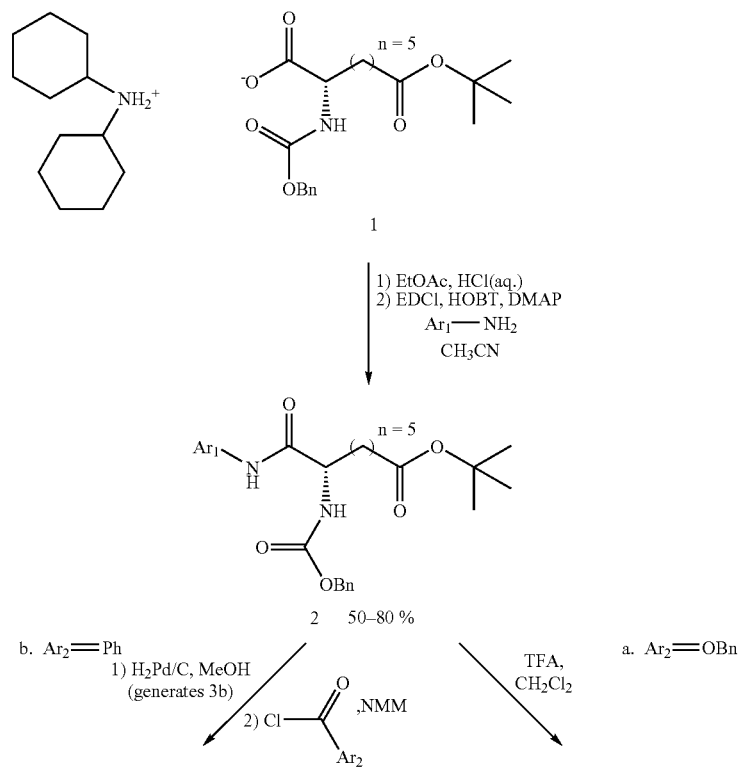

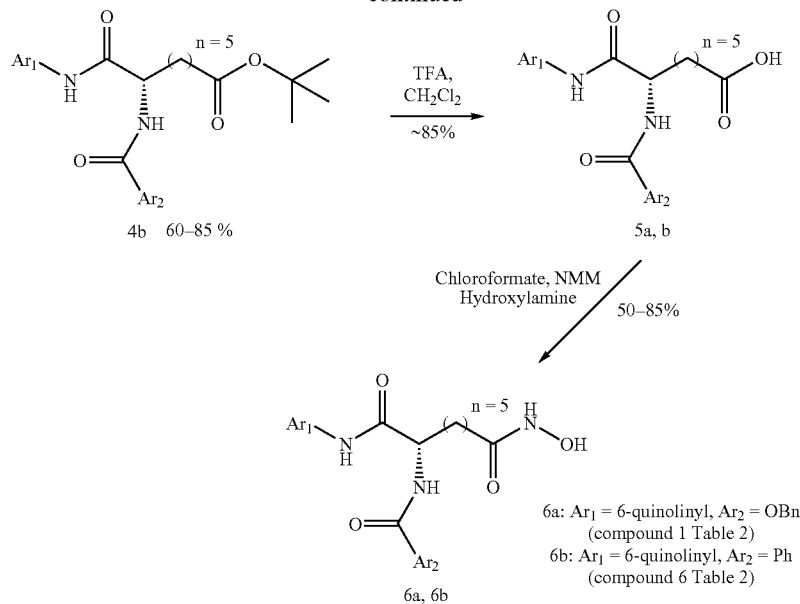

COMPOUND 1:

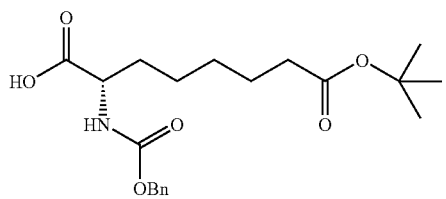

(7S)-7-BENZYLOXYCARBONYLAMINO-OCTANEDIOIC ACID 8-TERT-BUTYL ESTER (1)

To a slurry of commercially available dicyclohexylamine salt of N-Cbz-(L)-Asu(OtBu) (9.0 g, 16.1 mmol) in EtOAc (500 mL) was added 1N HCl (160 mL). The resultant slurry was shook in a separatory funnel and filtered. The aqueous layer was extracted further with EtOAc, and the combined organic layers were washed with 1N HCl (60 mL), and H2O (60 mL). The organic layer was dried, filtered, and concentrated under reduced pressure to yield a clear oil 6.2 g, which was used without further purification.

COMPOUND 2:

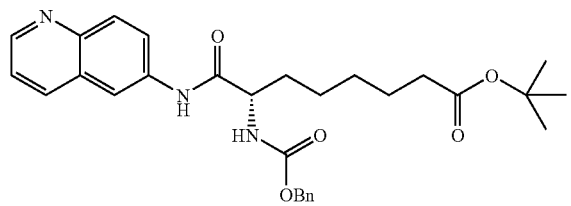

(7S)-7-BENZYLOXYCARBONYLAMINO-7-(QUINOLIN-6-YLCARBAMOYL)-HEPTANOIC ACID TERT-BUTYL ESTER (2)

(7S)-7-Benzyloxycarbonylamino-octanedioic acid 8-tert-butyl ester (10.0 g, 26.3 mmol), 6-aminoquinoline (4.02 g, 27.9 mmol) and EDCI (6.07 g, 29.0 mmol) were dissolved in 150 mL anhydrous $CH_3CN$. The solution was stirred at RT for 2 h. The solvent was removed under reduced pressure, and the residue was dissolved in 500 mL EtOAc and washed with 1 M HCl (200×3) and water (100×2). The organic layer was dried over anhydrous $Na_2SO_4$ Removal of solvent gave 16 g crude product. The pure compound 9.0 g was obtained with column separation (ethyl acetate as eluent) in 68% as a thick oil. $^1H$ NMR ($CDCl_3$) δ 8.80 (1H, d), 8.70 (1H, s), 8.30 (1H, d), 8.00 (2H, t), 7.56–7.20 (7H), 5.40 (1H, d), 5.08 (2H, s), 4.38 (1H, m), 2.20 (2H, t), 2.0–1.6 (17H, m). MS (ESI): ($MH^+$) 506.3.

COMPOUND 3b:

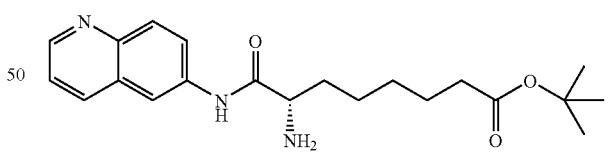

(7S)-7-AMINO-7-(QUINOLIN-6-YLCARBAMOYL)-HEPTANOIC ACID TERT-BUTYL ESTER (3b)

To a stirring solution of (7S)-7-benzyloxycarbonylamino-7-(quinolin-6-ylcarbamoyl)-heptanoic acid tert-butyl ester (11.0 g, 21.8 mmol) in EtOAc and MeOH was added 10% Pd/C. The reaction was charged with $H_2$, degassed and refilled with hydrogen three times. The slurry was stirred at RT for 2 h at balloon pressure, then filtered through a plug of Celite, and solvent was removed under reduced pressure. The hydrogenolysis of the ester yielded 8.0 g (99%) of a thick oil solid after 19 h. ¹H NMR (CDCl₃) δ 8.9–7.3 (7H, m), 3.96 (1H, m), 2.31 (2H, t), 2.0–1.2 (17H, m). MS (ESI): (MH⁺) 372.2.

COMPOUND 4b:

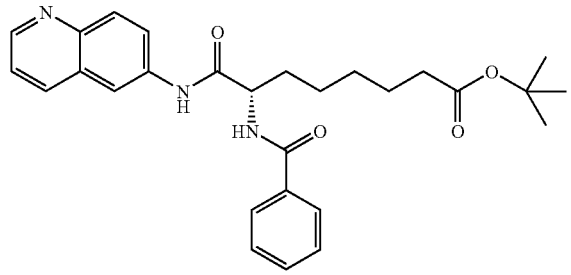

(7S)-7-BENZOYLAMINO-7-(QUINOLIN-6-YL-CARBAMOYL)-HEPTANOIC ACID TERT-BUTYL ESTER (4b)

To a stirring solution of (7S)-7-amino-7-(quinolin-6-ylcarbamoyl)-heptanoic acid tert-butyl ester (8.0 g, 21.6 mmol) in dry MeCN (100 mL) and to this solution was added benzoyl chloride (2.78 mL, 23.8 mmol) and triethylamine (6.1 mL, 43.2 mmol). The solution was stirred at 0° C. for 1 h, then at RT for 2 h. The solvent was removed, and residue was dissolved in 400 mL EtOAc, and stirred with 100 mL 0.5 M NaHCO₃ for 1 h. The aqueous layer was removed, and the organic layer was washed with 100 mL 0.5 M NaHCO₃, then with 50 mL water. The solution was dried over anhydrous Na₂SO₄. The product (8.1 g) was obtained after column purification (EtOAc as eluent) in 78.8% yield as a thick oil. ¹H NMR (CDCl₃) δ 9.40 (1H, s), 8.80 (1H, d), 8.22 (1H, d), 8.0–7.0 (10H, m), 5.0 (1H, m), 2.2–1.2 (19H, m). MS (ESI): (MH⁺) 476.1.

COMPOUND 5b:

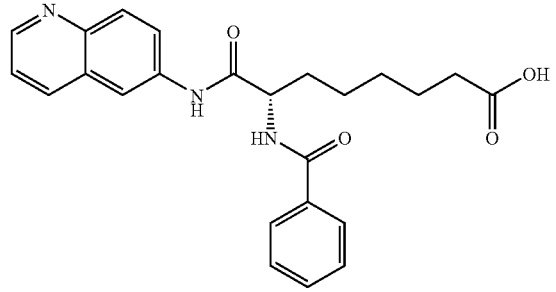

(7S)-7-BENZOYLAMINO-7-(QUINOLIN-6-YL-CARBAMOYL)-HEPTANOIC ACID (5b)

TFA deprotection of the t-butyl ester (8.45 g, 17.8 mmol) in CH₂Cl₂ (40 mL) and TFA (10 mL) was stirred for 24 h. The solvent was removed under reduced pressure and the residue was dissolved in 300 mL EtOAc. The solution was adjusted to pH 4 with aq. NaHCO₃, and the organic phase was collected. The aqueous phase was extracted with ethyl acetate (2×100 mL). The combined ethyl acetate fractions were dried over anhydrous Na₂SO₄. The solvent was removed, and the resulting residue was stirred with methylene chloride to give an off white solid 6.9 g with yield of 93.5% ¹H NMR (DMSO-d6) δ 10.6 (1H, s), 8.82 (1H, d), 8.76 (1H, d), 8.4–7.4 (10H, m), 4.60 (1H, m), 2.2 (2H, t), 1.8–1.2 (8H, m). MS (ESI): (MH⁺) 420.1.

COMPOUND 5a:

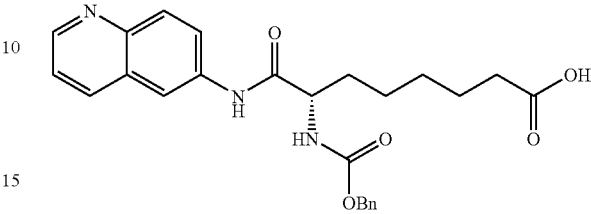

(7S)-7-BENZYLOXYCARBONYLAMINO-7-(QUINOLIN-6-YLCARBAMOYL)-HEPTANOIC ACID (5a)

The same procedure as for the preparation of Compound 5a ((7S)-7-Benzoylamino-7-(quinolin-6-ylcarbamoyl)-heptanoic acid) was employed. TFA deprotection of the t-butyl ester (9.0 g, 17.8 mmol) yielded 7.4 g (92.5%) of an off white solid after 24 h. ¹H NMR (DMSO) δ 10.6 (1H, s), 8.82 (1H, d), 8.76 (1H, d), 8.4–7.4 (10H, m), 5.0 (2H, s), 4.20 (1H, m), 2.4 (2H, t), 1.8–1.2 (8H, m). MS (ESI): (MH⁺) 450.2.

COMPOUND 6b:

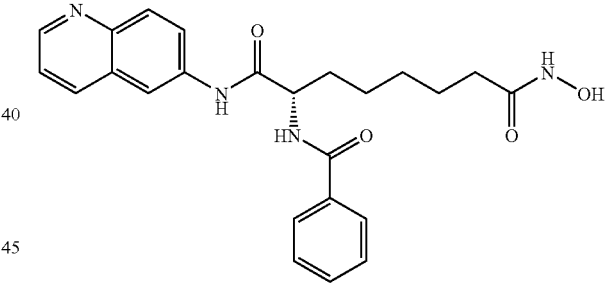

(2S)-2-BENZOYLAMINO-OCTANEDIOIC ACID 8-HYDROXYAMIDE 1-QUINOLIN-6-YLAMIDE (6b)

The acid (2.33 g, 5.57 mmol) was mixed with iso-butylchloroformate (2.19 mL, 16.7 mmol), NMM (2.1 mL, 18.9 mmol), and 4.0 equiv. of hydroxylamine (prepared as previously stated with excess hydroxylamine.HCl and NaOH) in MeCN and yielded a solid after solvent removal. The solid was stirred with 30 mL EtOAc and aq. sodium bicarbonate (30 mL) for 20 min. The solid was triturated with EtOAc (60 mL), xylene/MeOH (100 mL, 2:1), chloroform (60 mL), MeCN (100 mL), xylene/MeOH (100 mL, 2:1) and acetone (60 mL) respectively yielding a white solid (58.7%) with purity over 97%. ¹H NMR (CDCl₃) δ 10.4 (1H, d), 8.8–7.4 (13H, m), 4.60 (1H, m), 2.45 (1H, s), 1.9–1.3 (9H, m). MS (ESI): (MH⁺) 435.1.

COMPOUND 6a:

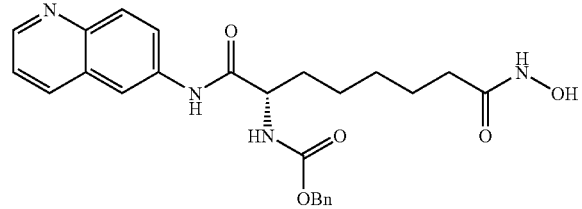

(S)-[6-HYDROXYCARBAMOYL-1-(QUINOLIN-6-YLCARBAMOYL)-HEXYL]-CARBAMIC ACID BENZYL ESTER (6a)

The acid (2.5 g, 5.57 mmol) was mixed with iso-butylchloroformate (2.19 mL, 16.7 mmol), NMM (2.1 mL, 18.9 mmol), and 4.0 equiv. of hydroxylamine hydroxylamine (prepared as previously stated with excess hydroxylamine HCl and NaOH) in MeCN and yielded a solid after solvent removal. The solid was stirred with 30 mL EtOAc and aq. sodium bicarbonate (30 mL) for 20 min. The solid was triturated with EtOAc (60 mL), xylene/MeOH (100 mL, 2:1), chloroform (60 mL), MeCN (100 mL), xylene/MeOH (100 mL, 2:1) and acetone (60 mL) respectively yielding a white solid (67.6%) with purity over 97%. $^1$H NMR (DMSO) δ 10.4 (1H, d), 8.8–7.3 (13H, m), 5.04 (2H, s), 4.20 (1H, m), 2.45 (2H, t), 1.9–1.2 (8H, m). MS (ESI): (MH$^+$) 465.4.

Alternative Synthesis

An alterative synthesis was developed to reduce the number of synthetic steps, and reduce the overall cost of the reaction pathway. The synthesis started with the Boc-protected methyl ester amino-suberate I (Scheme 2). Amide formation was carried out using standard peptide coupling methodology. TFA deprotection yielded the amine-TFA salt, which was acylated using the requisite acid chloride, affording III. Formation of IV was accomplished in one step with methyl-ester III and hydroxylamine. Compound 6 was prepared according to the aternate synthesis and isolated as the racemic mixture due to the use of racemic starting material (1).

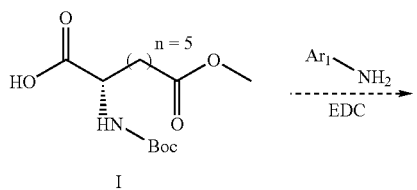

I

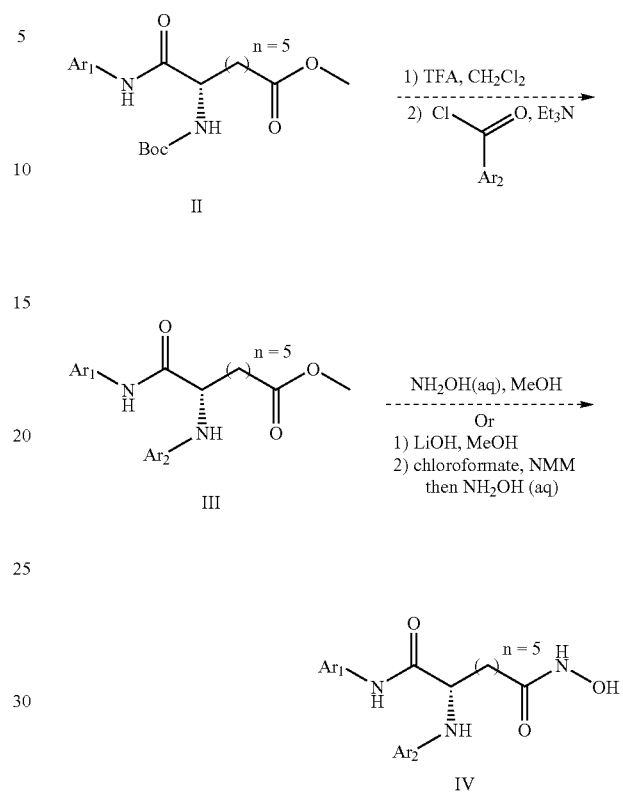

EXAMPLE 2

HDAC Inhibition by Novel Compounds

HDAC1-Flag Assay:

Novel compounds were tested for their ability to inhibit histone deacetylase, subtype 1 (HDAC1) using an in vitro deacetylation assay. The enzyme source for this assay was an epitope-tagged human HDAC1 complex immuno-purified from stably expressing mammalian cells. The substrate consisted of a commercial product containing an acetylated lysine side chain (Biomol, Plymouth Meeting, Pa.). Upon deacetylation of the substrate by incubation with the purified HDAC1 complex, a fluorophore is produced that is directly proportional to the level of deacetylation. Using a substrate concentration at the Km for the enzyme preparation, the deacetylation assay was performed in the presence of increasing concentrations of novel compounds to semi-quantitatively determine the concentration of compound required for 50% inhibition (IC$_{50}$) of the deacetylation reaction.

Results:

Table 2 below shows the chemical structures and HDAC enzymatic assay results for a selection of novel compounds designed and synthesized in accordance with the present invention. Additional compounds are shown in Table 4, below.

TABLE 2

| No. | Structure | Mol. Formula | MW | HDAC Inhibition IC50, nM |
|---|---|---|---|---|
| 6a | 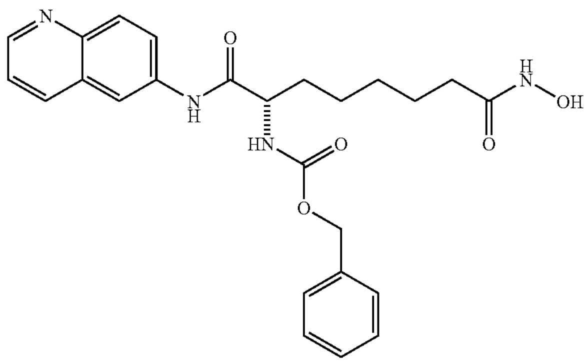 | C<sub>25</sub>H<sub>28</sub>N<sub>4</sub>O<sub>5</sub> | 464.5 | 5.9 |
| 2 | 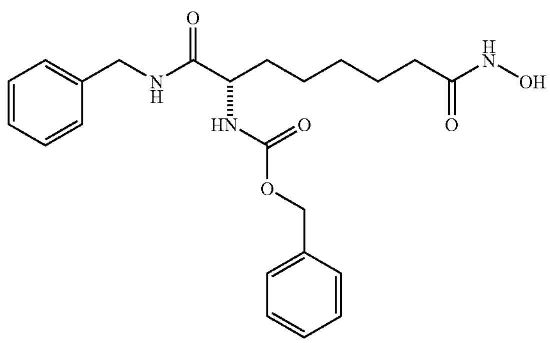 | C<sub>23</sub>H<sub>29</sub>N<sub>3</sub>O<sub>5</sub> | 427.5 | 37.4 |
| 3 | 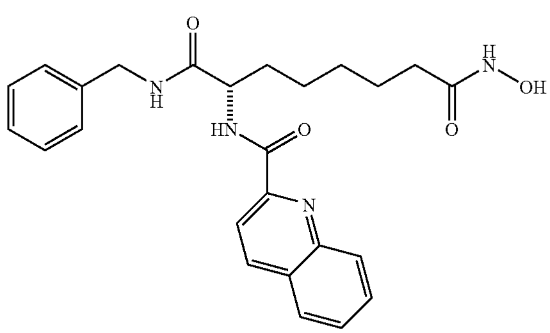 | C<sub>25</sub>H<sub>28</sub>N<sub>4</sub>O<sub>4</sub> | 448.5 | 52.7 |
| 4 | 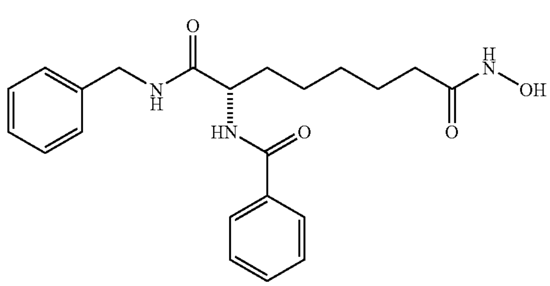 | C<sub>25</sub>H<sub>27</sub>N<sub>3</sub>O<sub>4</sub> | 397.5 | 73.0 |

TABLE 2-continued
| No. | Structure | Mol. Formula | MW | HDAC Inhibition IC50,nM |
|---|---|---|---|---|
| 5 | 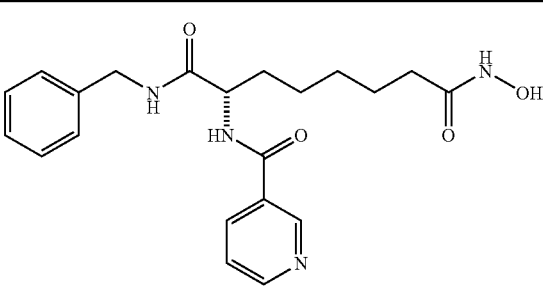 | C21H26N4O4 | 398.5 | 149.8 |
| 6b | 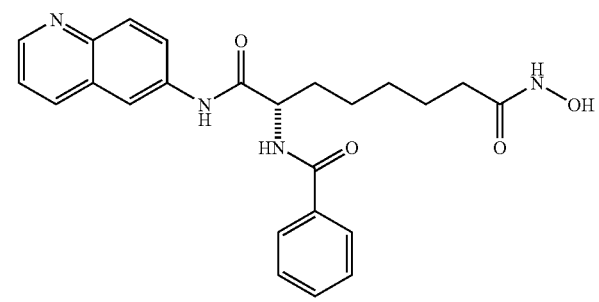 | C24H26N4O4 | 434.5 | 1.8 |
| 7 | 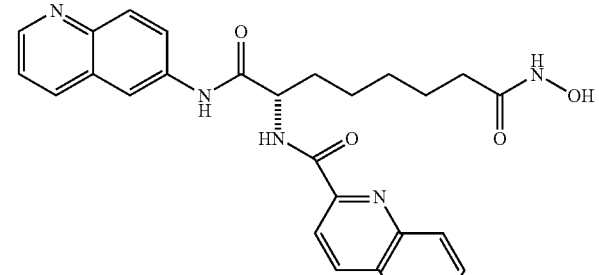 | C27H27N5O4 | 485.5 | 54.5 |
| 8 | 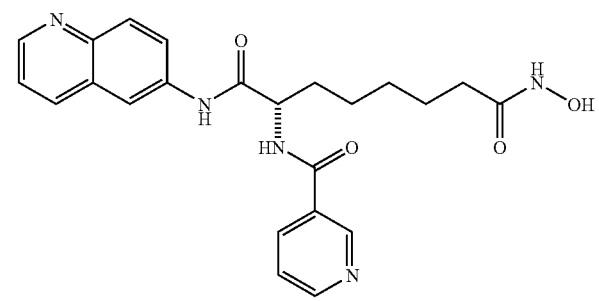 | C23H25N5O4 | 435.5 | 1.6 |

TABLE 2-continued

| No. | Structure | Mol. Formula | MW | HDAC Inhibition IC50,nM |
|---|---|---|---|---|
| 9 | 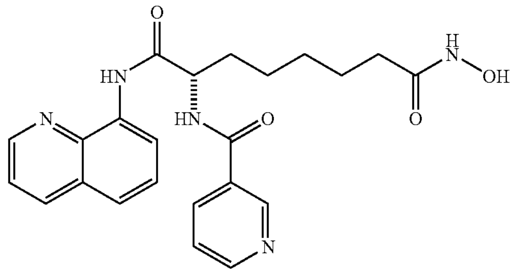 | $C_{23}H_{25}N_5O_4$ | 435.5 | 4.1 |
| 10 | 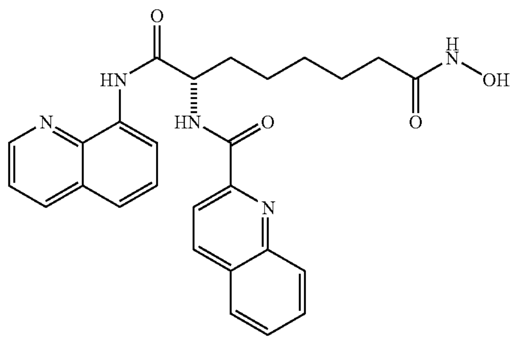 | $C_{27}H_{27}N_5O_4$ | 485.5 | 41.8 |
| 11 | 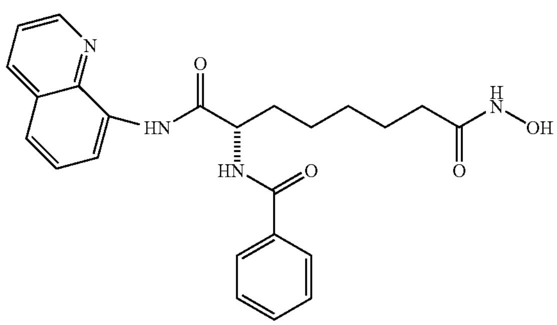 | $C_{24}H_{26}N_4O_4$ | 434.5 | 12.7 |

EXAMPLE 3

Proliferation Assay

Proliferation

The novel compounds of the present invention were tested for their ability to inhibit growth of the human bladder carcinoma cell line, T24. Cells were treated with compounds for 72 hours, lysed by freeze/thaw to expose the DNA, and then the DNA was quantitated using the intercalating dye, bisbenzamide (Sigma). Fluorescent intensity (ex 350λ em 460λ) was directly proportional to the number of cells per well. Fluorescence values from vehicle-treated cells were determined and used as 100%. The concentration of compound required to inhibit cell growth by 50% was determined and is reported in Table 3.

Results:

The results of the T24 cell-based proliferation assay from a select group of novel compounds are summarized in Table 3 below:

| Compound No. | Cell Growth Inhbition, $IC_{50}$ |
|---|---|
| 6a | 0.2 |
| 2 | 1.4 |
| 3 | 1.7 |
| 4 | 3.2 |
| 5 | 9.2 |
| 6b | 0.2 |
| 7 | 0.6 |
| 8 | 1.8 |
| 9 | 0.4 |
| 10 | 1.4 |
| 11 | 0.3 |

TABLE 4

| No. | Structure | Molecular Formula | MW | HDAC inhibition IC50(nM) |
|---|---|---|---|---|
| 12 | 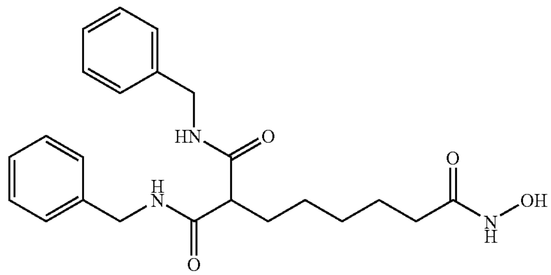 | $C_{23}H_{29}N_3O_4$ | 411.4998 | 156 + 22.6 (n = 2) |
| 13 | 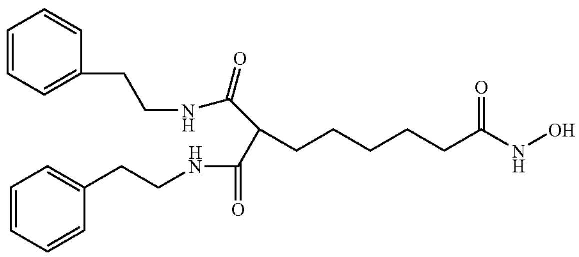 | $C_{25}H_{33}N_3O_4$ | 439.5534 | 185.5 + 21.9 (n = 2) |

While this invention has been particularly shown an described with references to preferred embodiments thereof, it will be understood by those skilled in the art that various changes in form and details may be made therein without departing from the scope of the invention encompassed by the appended claims.

What is claimed is:

1. A compound represented by the following structural formula:

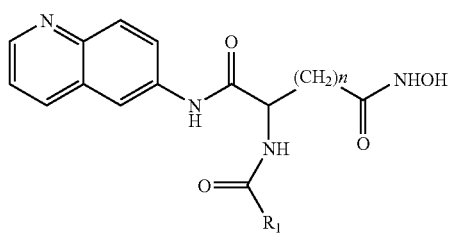

or stereoisomers or pharmaceutically acceptable salts, solvates or hydrates thereof, wherein:

$R_1$ is a substituted or unsubstituted pyridyl group, phenyl group, quinolinyl group, isoquinolinyl group, or arylalkoxy group; and n is an integer from 3 to 10.

2. A compound represented by the following structural formula:

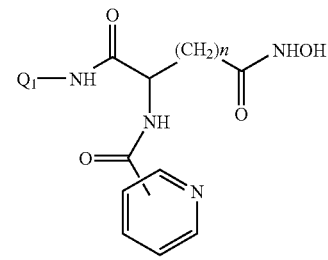

or stereoisomers or pharmaceutically acceptable salts, solvates or hydrates thereof, wherein:

$Q_1$ is a substituted or unsubstituted quinolinyl or isoquinolinyl group;

n is an integer from 3 to 10.

3. A compound represented by the following structural formula:

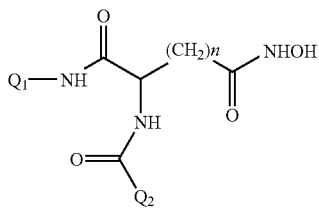

or stereoisomers or pharmaceutically acceptable salts, solvates or hydrates thereof, wherein:

$Q_1$ is a substituted or unsubstituted quinolinyl or isoquinolinyl group;

$Q_2$ is a 2-quinolinyl group; and n is an integer from 3 to 10.

4. The compound of claim 1, wherein n is 5.
5. The compound of claim 1, wherein $R_1$ is a substituted or unsubstituted phenyl group.
6. The compound of claim 5, wherein $R_1$ is an unsubstituted phenyl group.
7. The compound of claim 6, wherein n is 5.
8. The compound of claim 1, wherein $R_1$ is an unsubstituted pyridyl group.
9. The compound of claim 8, wherein $R_1$ is β-pyridyl.
10. The compound of claim 9, wherein n is 5.
11. The compound of claim 1, wherein $R_1$ is an unsubstituted quinolinyl group.
12. The compound of claim 11, wherein $R_1$ is a 2-quinolinyl group.
13. The compound of claim 12, wherein n is 5.
14. The compound of claim 1, wherein $R_1$ is a substituted or unsubstituted arylalkyloxy group.
15. The compound of claim 14, wherein $R_1$ is substituted or unsubstituted benzyloxy group.
16. The compound of claim 15, wherein $R_1$ is an unsubstituted benzyloxy group.
17. The compound of claim 16, wherein n is 5.
18. The compound of claim 2, wherein $Q_1$ is an 8-quinolinyl group.
19. The compound of claim 2, wherein the pyridyl group is β-pyridyl.
20. The compound of claim 19 wherein $Q_1$ is an 8-quinolinyl group.
21. The compound of claim 20, wherein n is 5.
22. The compound of claim 3, wherein $Q_1$ is an 8-quinolinyl group.
23. The compound of claim 3, wherein $Q_2$ is a 2-quinolinyl group.
24. The compound of claim 23, wherein $Q_1$ is an 8-quinolinyl group.
25. The compound of claim 24, wherein is 5.
26. A pharmaceutical composition comprising a pharmaceutically effective amount of the compound of any of claims 1, 2 and 3, and a pharmaceutically acceptable carrier.
27. A method of treating cancer in a subject in need of treatment comprising administering to said subject a therapeutically effective amount the compound of any one of claims 1, 2 and 3 wherein the effective amount is sufficient to inhibit the activity of histone deacetylase.
28. A method of selectively inducing terminal differentiation of neoplastic cells and thereby inhibiting proliferation of such cells which comprises contacting the cells under suitable conditions with an effective amount of the compound of any one of claims 1, 2 and 3.
29. A method of selectively inducing cell growth arrest of neoplastic cells and thereby inhibiting proliferation of such cells which comprises contacting the cells under suitable conditions with an effective amount of the compound of any one of claims 1, 2 and 3.
30. A method of selectively inducing apoptosis of neoplastic cells and thereby inhibiting proliferation of such cells which comprises contacting the cells under suitable conditions with an effective amount of the compound of any one of claims 1, 2 and 3.
31. A method of inducing terminal differentiation of tumor cells in a tumor comprising contacting the cells with an effective amount of the compound of any one of claims 1, 2 and 3 where wherein the effective amount is sufficient to inhibit the activity of histone deacetylase.
32. A method of inhibiting the activity of histone deacetylase comprising contacting the histone deacetylase with an effective amount of the compound of any one of claims 1, 2 and 3 so as to inhibit the activity of histone acetylase.

33. The compound of claim 1 having the structure:

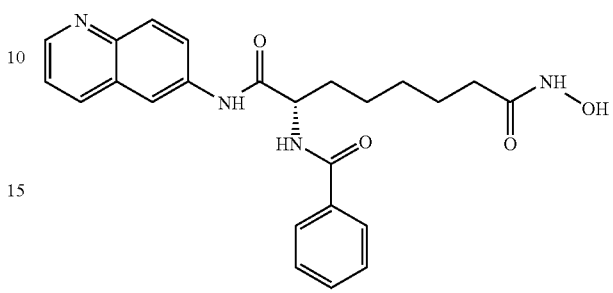

or a pharmaceutically acceptable salt or an enantiomer thereof.

34. The compound of claim 1 having the structure:

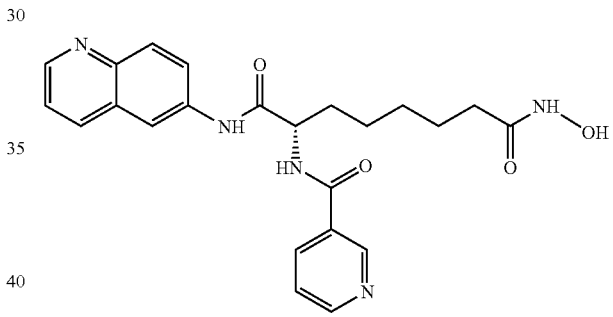

or a pharmaceutically acceptable salt or an enantiomer thereof.

35. The compound of claim 1 having the structure:

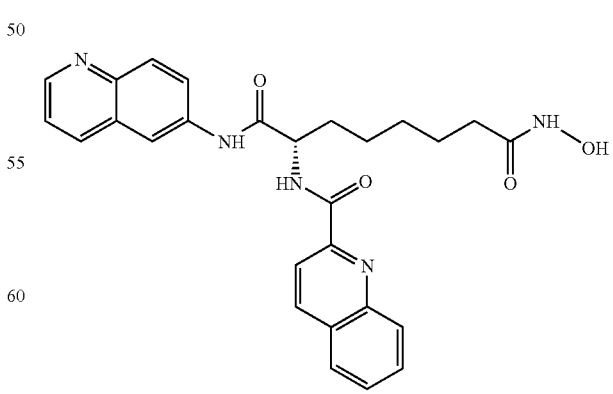

or a pharmaceutically acceptable salt or an enantiomer thereof.

36. The compound of claim 1 having the structure:
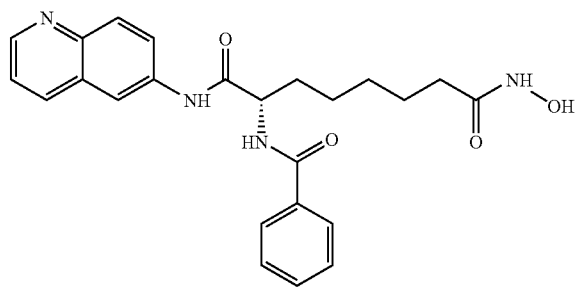
or a pharmaceutically acceptable salt or an enantiomer thereof.
37. The compound of claim 2 having the structure:
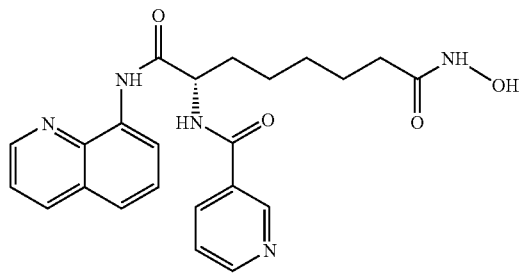
or a pharmaceutically acceptable salt or an enantiomer thereof.
38. The compound of claim 3 having the structure:
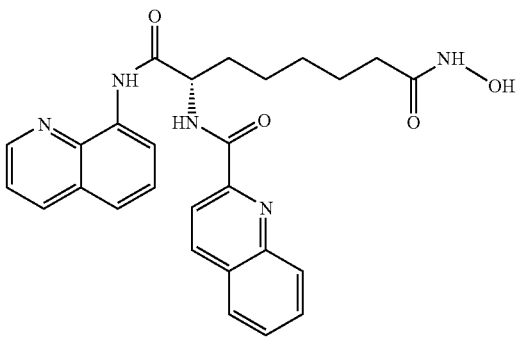
or a pharmaceutically acceptable salt or an enantiomer thereof.
* * * * *

UNITED STATES PATENT AND TRADEMARK OFFICE
CERTIFICATE OF CORRECTION

PATENT NO. : 7,199,134 B2  
APPLICATION NO. : 10/817688  
DATED : April 3, 2007  
INVENTOR(S) : Breslow et al.

Page 1 of 1

It is certified that error appears in the above-identified patent and that said Letters Patent is hereby corrected as shown below:

At Column 43, lines 2-15, Claim 36, the chemical structure

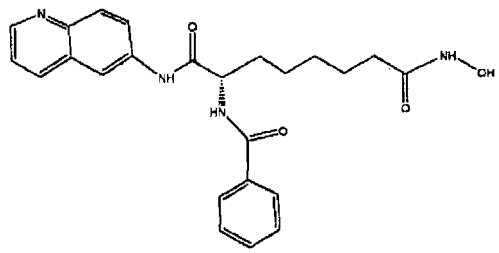

" "

should be replaced with

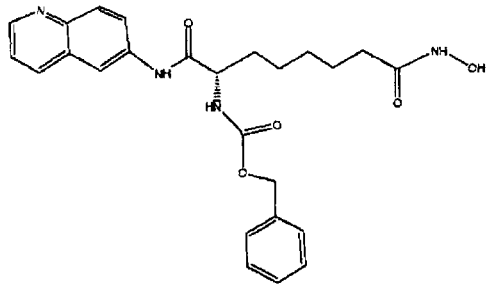

-- --.

Signed and Sealed this  
Fourth Day of January, 2011

David J. Kappos  
*Director of the United States Patent and Trademark Office*